United States Patent
Batra et al.

(10) Patent No.: US 12,168,071 B2
(45) Date of Patent: Dec. 17, 2024

(54) TREPROSTINIL DERIVATIVES AND THEIR USE IN PHARMACEUTICAL COMPOSITIONS

(71) Applicant: United Therapeutics Corporation, Silver Spring, MD (US)

(72) Inventors: Hitesh Batra, Herndon, VA (US); Liang Guo, Vienna, VA (US); Patrick Poisson, Chapel Hill, NC (US); Susovan Jana, Rockville, MD (US)

(73) Assignee: United Therapeutics Corporation, Silver Spring, MD (US)

( * ) Notice: Subject to any disclaimer, the term of this patent is extended or adjusted under 35 U.S.C. 154(b) by 0 days.

(21) Appl. No.: 17/685,038

(22) Filed: Mar. 2, 2022

(65) Prior Publication Data

US 2022/0280430 A1    Sep. 8, 2022

Related U.S. Application Data

(60) Provisional application No. 63/156,110, filed on Mar. 3, 2021.

(51) Int. Cl.
| | |
|---|---|
| *C07D 471/04* | (2006.01) |
| *A01N 43/90* | (2006.01) |
| *A61K 9/00* | (2006.01) |
| *A61K 9/14* | (2006.01) |
| *A61K 31/5575* | (2006.01) |
| *A61K 45/06* | (2006.01) |

(52) U.S. Cl.
CPC .............. *A61K 9/14* (2013.01); *A61K 9/0075* (2013.01); *A61K 31/5575* (2013.01); *A61K 45/06* (2013.01)

(58) Field of Classification Search
CPC .... A61K 9/14; A61K 9/0075; A61K 31/5575; A61K 45/06; A61K 31/495; A61K 47/542; A61P 9/12
See application file for complete search history.

(56) References Cited

U.S. PATENT DOCUMENTS

| | | | |
|---|---|---|---|
| 4,306,075 A | 12/1981 | Aristoff | |
| 5,153,222 A | 10/1992 | Tadepalli et al. | |
| 5,234,953 A | 8/1993 | Crow et al. | |
| 6,054,486 A | 4/2000 | Crow et al. | |
| 6,441,245 B1 | 8/2002 | Moriarty et al. | |
| 6,521,212 B1 | 2/2003 | Cloutier et al. | |
| 6,528,688 B2 | 3/2003 | Moriarty et al. | |
| 6,700,025 B2 | 3/2004 | Moriarty et al. | |
| 6,756,033 B2 | 6/2004 | Cloutier et al. | |
| 6,756,117 B1 | 6/2004 | Barnes | |
| 6,803,386 B2 | 10/2004 | Shorr et al. | |
| 6,809,223 B2 | 10/2004 | Moriarty et al. | |
| 7,199,157 B2 | 4/2007 | Wade et al. | |
| 7,305,986 B1 | 12/2007 | Steiner et al. | |
| 7,384,978 B2 | 6/2008 | Phares et al. | |
| 7,417,070 B2 | 8/2008 | Phares et al. | |
| 7,464,706 B2 | 12/2008 | Steiner et al. | |
| 7,544,713 B2 | 6/2009 | Phares et al. | |
| 7,879,909 B2 | 2/2011 | Wade et al. | |
| 7,999,007 B2 | 8/2011 | Jeffs et al. | |
| 8,232,316 B2 | 7/2012 | Phares et al. | |
| 8,242,305 B2 | 8/2012 | Batra et al. | |
| 8,252,839 B2 | 8/2012 | Phares et al. | |
| 8,349,892 B2 | 1/2013 | Phares | |
| 8,350,079 B2 | 1/2013 | Walsh | |
| 8,410,169 B2 | 4/2013 | Phares et al. | |
| 8,461,393 B2 | 6/2013 | Sharma | |
| 8,481,782 B2 | 7/2013 | Batra et al. | |
| 8,497,393 B2 | 7/2013 | Batra et al. | |
| 8,499,757 B2 | 8/2013 | Smutney et al. | |
| 8,536,363 B2 | 9/2013 | Phares et al. | |
| 8,563,614 B2 | 10/2013 | Wade et al. | |
| 8,609,728 B2 | 12/2013 | Rothblatt et al. | |
| 8,636,001 B2 | 1/2014 | Smutney et al. | |
| 8,653,137 B2 | 2/2014 | Jeffs et al. | |
| 8,658,694 B2 | 2/2014 | Jeffs et al. | |
| 8,747,897 B2 | 6/2014 | Kidane et al. | |
| 8,765,813 B2 | 7/2014 | Wade et al. | |
| 8,940,930 B2 | 1/2015 | Batra et al. | |
| 9,029,607 B2 | 5/2015 | Mcgowan et al. | |
| 9,050,311 B2 | 6/2015 | Phares et al. | |
| 9,156,786 B2 | 10/2015 | Batra et al. | |
| 9,199,908 B2 | 12/2015 | Phares et al. | |
| 9,255,064 B2 | 2/2016 | Malinin et al. | |
| 9,278,901 B2 | 3/2016 | Phares et al. | |
| 9,278,902 B2 | 3/2016 | Tang et al. | |
| 9,278,903 B2 | 3/2016 | Tang et al. | |

(Continued)

FOREIGN PATENT DOCUMENTS

| | | |
|---|---|---|
| WO | WO-00/57701 A1 | 10/2000 |
| WO | WO-2005/007081 A3 | 1/2005 |
| WO | WO-2016/038532 A1 | 3/2016 |
| WO | WO-2016/055819 A1 | 4/2016 |
| WO | WO-2016/081658 A1 | 5/2016 |
| WO | WO-2016/105538 A1 | 6/2016 |

(Continued)

OTHER PUBLICATIONS

U.S. Appl. No. 17/549,573, filed Dec. 13, 2021, Phares et al.
Moriarty et al., "The Intramolecular Asymmetric Pauson-Khand Cyclization as a Novel and General Stereoselective Route to Benzindene Prostacyclins: Synthesis of UT-15 (Treprostinil)," J. Org. Chem., 2004, 69:1890-1902.
Sorbera et al., "UT-15. Treatment of Pulmonary Hypertension Treatment of Peripheral Vascular Disease," Drug of the Future, 2001, 26(4):364-374.

*Primary Examiner* — Mina Haghighatian
*Assistant Examiner* — Janice Y Silverman
(74) *Attorney, Agent, or Firm* — Foley & Lardner LLP

(57) ABSTRACT

Provided are treprostinil derivatives with a reduced ability to form undesired impurities in a pharmaceutical formulation, such as a dry powder formulation, further containing a carboxyl group containing inactive ingredient, such as fumaryl diketopiperazine.

21 Claims, 5 Drawing Sheets

(56) References Cited

U.S. PATENT DOCUMENTS

| | | |
|---|---|---|
| 9,339,507 B2 | 5/2016 | Olschewski et al. |
| 9,346,738 B2 | 5/2016 | Jain et al. |
| 9,358,240 B2 | 6/2016 | Olschewski et al. |
| 9,371,264 B2 | 6/2016 | Becker et al. |
| 9,388,154 B2 | 7/2016 | Yiannikouros et al. |
| 9,394,227 B1 | 7/2016 | Zhang et al. |
| 9,422,223 B2 | 8/2016 | Phares et al. |
| 9,469,600 B2 | 10/2016 | Malinin et al. |
| 9,505,737 B2 | 11/2016 | Becker et al. |
| 9,624,156 B2 | 4/2017 | Phares et al. |
| 9,643,911 B2 | 5/2017 | Zhang et al. |
| 9,701,611 B2 | 7/2017 | Batra et al. |
| 9,701,616 B2 | 7/2017 | Zhang et al. |
| 9,758,465 B2 | 9/2017 | Laing |
| 9,776,982 B2 | 10/2017 | Becker et al. |
| 9,845,305 B2 | 12/2017 | Becker et al. |
| 9,878,972 B2 | 1/2018 | Phares et al. |
| 9,957,200 B2 | 5/2018 | Beall et al. |
| 9,988,334 B2 | 6/2018 | Batra et al. |
| 10,010,518 B2 | 7/2018 | Malinin et al. |
| 10,053,414 B2 | 8/2018 | Zhang et al. |
| 10,246,403 B2 | 4/2019 | Zhang et al. |
| 10,343,979 B2 | 7/2019 | Malinin et al. |
| 10,344,012 B2 | 7/2019 | Becker et al. |
| 10,450,290 B2 | 10/2019 | Becker et al. |
| 10,464,877 B2 | 11/2019 | Zhang et al. |
| 10,464,878 B2 | 11/2019 | Zhang et al. |
| 10,526,274 B2 | 1/2020 | Malinin et al. |
| 10,703,706 B2 | 7/2020 | Zhang et al. |
| 10,752,733 B2 | 8/2020 | Ishihara |
| 2005/0085540 A1 | 4/2005 | Phares et al. |
| 2008/0200449 A1 | 8/2008 | Olschewski et al. |
| 2008/0280986 A1 | 11/2008 | Wade et al. |
| 2009/0036465 A1 | 2/2009 | Roscigno et al. |
| 2009/0124697 A1 | 5/2009 | Cloutier et al. |
| 2012/0197041 A1 | 8/2012 | Batra et al. |
| 2013/0184295 A1 | 7/2013 | Sprague et al. |
| 2013/0331593 A1 | 12/2013 | Mcgowan et al. |
| 2014/0024856 A1 | 1/2014 | Giust et al. |
| 2014/0275262 A1 | 9/2014 | Phares et al. |
| 2014/0275616 A1 | 9/2014 | Batra et al. |
| 2014/0323567 A1 | 10/2014 | Laing |
| 2015/0148414 A1 | 5/2015 | Malinin et al. |
| 2015/0299091 A1 | 10/2015 | Batra et al. |
| 2015/0315114 A1 | 11/2015 | Hering et al. |
| 2015/0328232 A1 | 11/2015 | Malinin et al. |
| 2015/0376106 A1 | 12/2015 | Batra et al. |
| 2016/0030355 A1 | 2/2016 | Kidane et al. |
| 2016/0030371 A1 | 2/2016 | Phares et al. |
| 2016/0045470 A1 | 2/2016 | Reddy et al. |
| 2016/0051505 A1 | 2/2016 | Phares et al. |
| 2016/0107973 A1 | 4/2016 | Batra et al. |
| 2016/0129087 A1 | 5/2016 | Christe et al. |
| 2016/0143868 A1 | 5/2016 | Olschewski et al. |
| 2016/0152548 A1 | 6/2016 | Gao et al. |
| 2016/0175319 A1 | 6/2016 | Freissmuth et al. |
| 2016/0243064 A1* | 8/2016 | Trehan ............... A61K 9/2853 |
| 2017/0095432 A1 | 4/2017 | Phares et al. |
| 2018/0153847 A1 | 6/2018 | Phares et al. |
| 2019/0321290 A1 | 10/2019 | Guarneri et al. |
| 2020/0338005 A1 | 10/2020 | Du et al. |
| 2021/0054009 A1 | 2/2021 | Phares et al. |
| 2021/0378996 A1 | 12/2021 | Batra et al. |

FOREIGN PATENT DOCUMENTS

| | | |
|---|---|---|
| WO | WO-2018/058124 A1 | 3/2018 |
| WO | WO-2019/237028 A1 | 12/2019 |
| WO | WO-2021/211916 A1 | 10/2021 |

\* cited by examiner

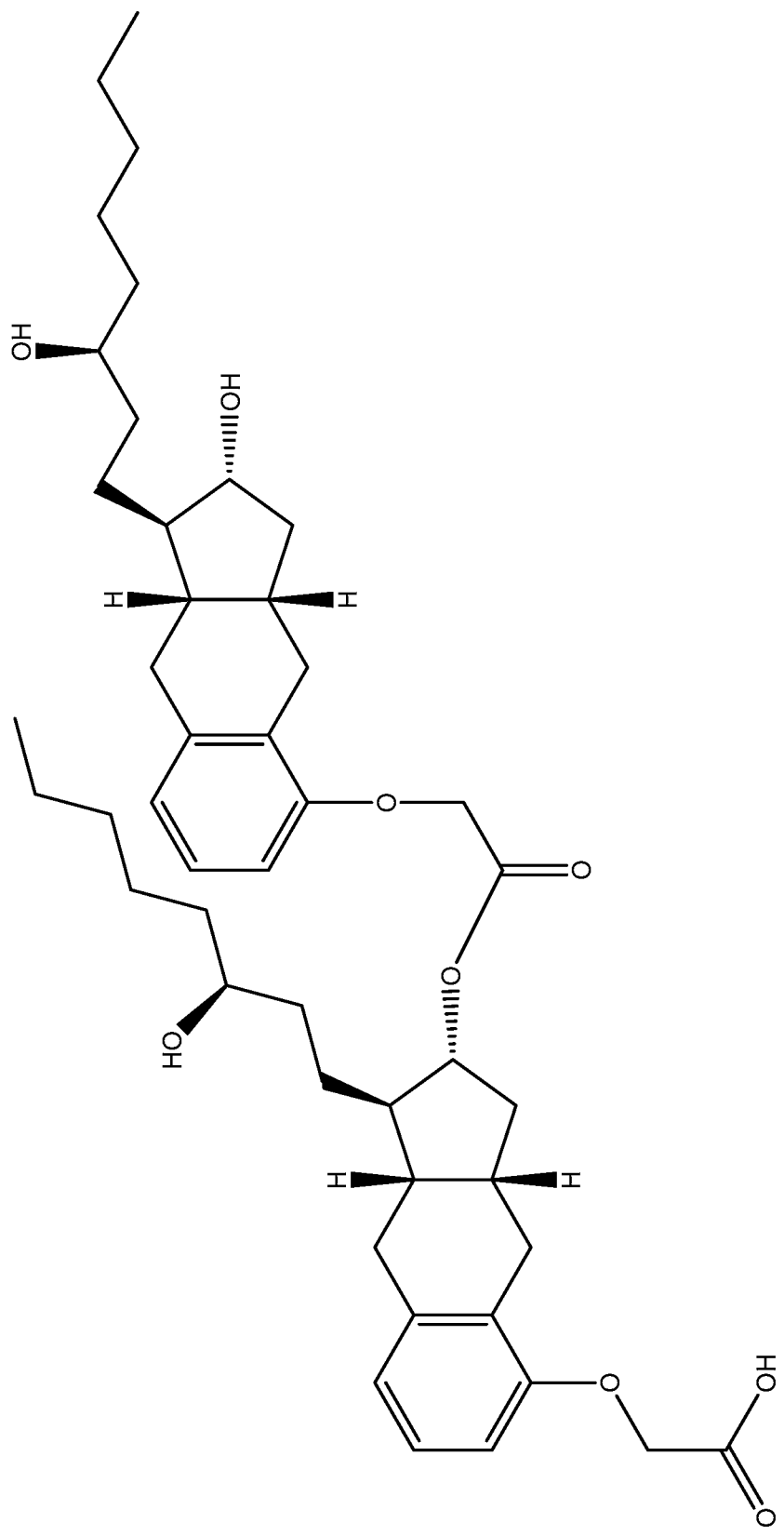
Figure 4: Treprostinil Ring Dimer

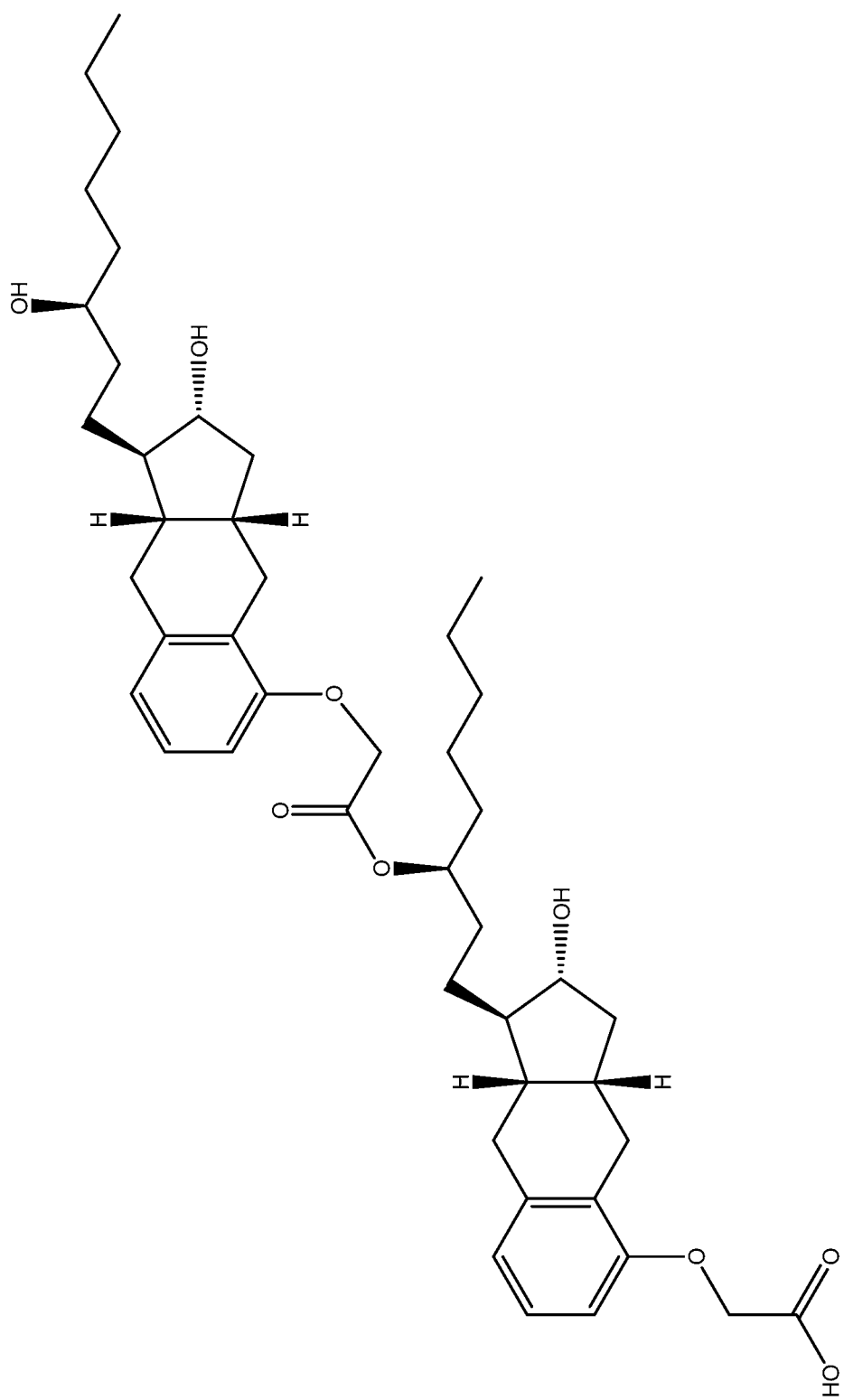
Figure 5: Treprostinil Side Chain Dimer

TREPROSTINIL DERIVATIVES AND THEIR USE IN PHARMACEUTICAL COMPOSITIONS

RELATED APPLICATIONS

The present application claims priority to U.S. provisional application No. 63/156,110 filed Mar. 3, 2021, which is incorporated herein by reference in its entirety.

FIELD

The present disclosure generally relates to treprostinil derivatives and more specifically, to treprostinil derivatives with a reduced ability to form undesired impurities in a pharmaceutical formulation and their methods of making and using.

SUMMARY

One embodiment is a powder formulation comprising (a) a treprostinil prodrug, a treprostinil salt or a salt of treprostinil prodrug and (b) fumaryl 2,5-diketopiperazine or (E)-3,6-bis[4-(N-carbonyl-2-propenyl)amidobutyl]-2,5-diketopiperazine (FDKP).

Another embodiment is a compound having the following formula:

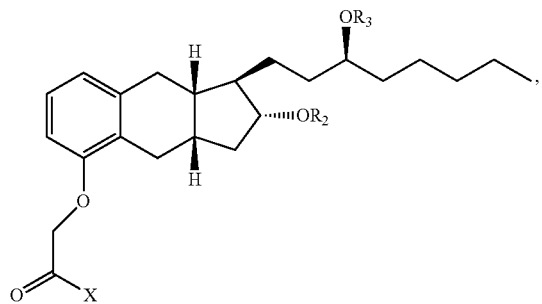

wherein $R_2$ is a first promoiety, $R_3$ is a second promoiety; and X is a salt moiety or a third promoiety; wherein each of $OR_2$ and $OR_3$ has a lower reactivity with a carboxyl group than that of the respective hydroxyl group of unsubstituted treprostinil and C=OX has a lower reactivity with hydroxyl than that of the carboxyl group of unsubstituted treprostinil.

FIGURES

Figure 1:
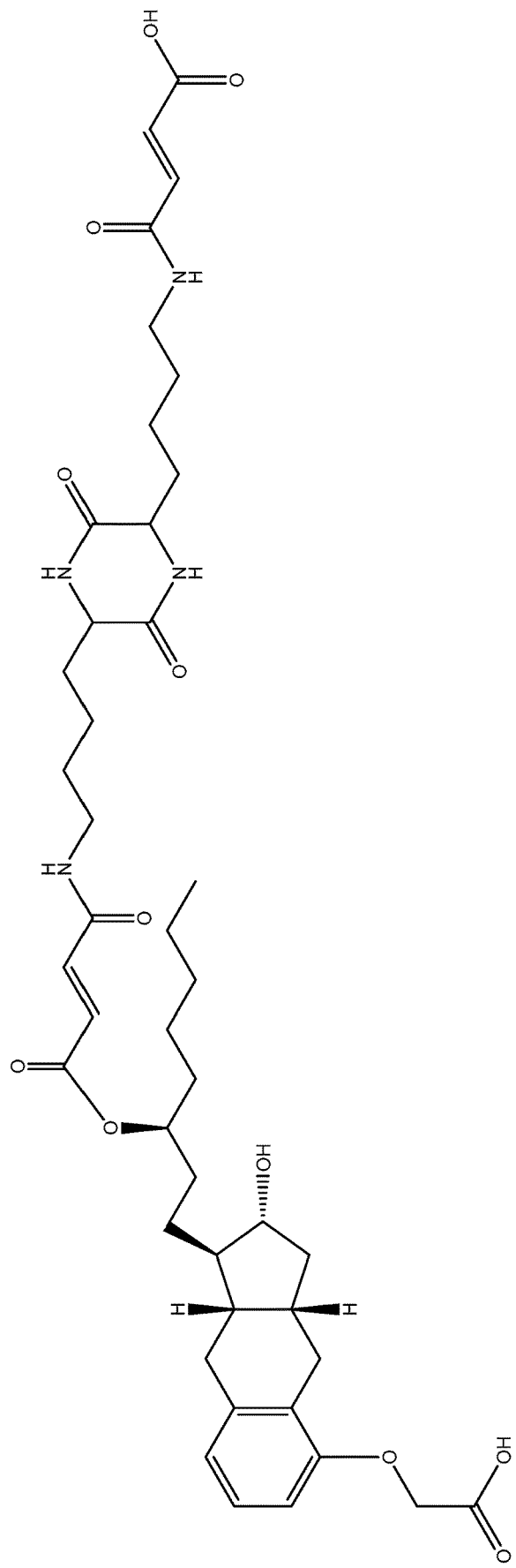
FIG. 1 shows an impurity, which may be formed via a reaction between a hydroxyl group on the alkyl side chain of a treprostinil molecule and FDKP.

FIG. 4 and FIG. 5 each show a treprostinil dimer impurity, which may be formed via a intermolecular reaction between a carboxyl group of a treprostinil molecule and a hydroxyl group of another Treprostinil.

DETAILED DESCRIPTION

As used herein and in the claims, the singular forms "a," "an," and "the" include the plural reference unless the context clearly indicates otherwise. Throughout this specification, unless otherwise indicated, "comprise," "comprises" and "comprising" are used inclusively rather than exclusively, so that a stated integer or group of integers may include one or more other non-stated integers or groups of integers. The term "of" is inclusive unless modified, for example, by "either." Thus, unless context indicates otherwise, the word "of" means any one member of a particular list and also includes any combination of members of that list. Other than in the operating examples, or where otherwise indicated, all numbers expressing quantities of ingredients or reaction conditions used herein should be understood as modified in all instances by the term "about."

Headings are provided for convenience only and are not to be construed to limit the invention in any way. Unless defined otherwise, all technical and scientific terms used herein have the same meaning as those commonly understood to one of ordinary skill in the art. The terminology used herein is for the purpose of describing particular embodiments only, and is not intended to limit the scope of the present invention, which is defined solely by the claims.

In order that the present disclosure can be more readily understood, certain terms are first defined. Additional definitions are set forth throughout the detailed description.

All numerical designations, e.g., pH, temperature, time, concentration, and molecular weight, including ranges, are approximations which are varied (+) or (−) by increments of 0.05%, 1%, 2%, 5%, 10% or 20%. It is to be understood, although not always explicitly stated that all numerical designations are preceded by the term "about." It also is to be understood, although not always explicitly stated, that the reagents described herein are merely exemplary and that equivalents of such are known in the art.

"HPLC" refers to high-performance liquid chromatography.

"NMR" refers to nuclear magnetic resonance.

As used herein, $C_m$-$C_n$, such as $C_1$-$C_{12}$, $C_1$-$C_8$, or $C_1$-$C_6$ when used before a group refers to that group containing m to n carbon atoms.

"Optionally substituted" refers to a group selected from that group and a substituted form of that group. Substituents may include any of the groups defined below. In one embodiment, substituents are selected from $C_1$-$C_{10}$ or $C_1$-$C_6$ alkyl, substituted $C_1$-$C_{10}$ or $C_1$-$C_6$ alkyl, $C_2$-$C_6$ alkenyl, $C_2$-$C_6$ alkynyl, $C_6$-$C_{10}$ aryl, $C_3$-$C_5$ cycloalkyl, $C_2$-$C_{10}$ heterocyclyl, $C_1$-$C_{10}$ heteroaryl, substituted $C_2$-$C_6$ alkenyl, substituted $C_2$-$C_6$ alkynyl, substituted $C_6$-$C_{10}$ aryl, substituted $C_3$-$C_8$ cycloalkyl, substituted $C_2$-$C_{10}$ heterocyclyl, substituted $C_1$-$C_{10}$ heteroaryl, halo, nitro, cyano, —$CO_2H$ or a $C_1$-$C_6$ alkyl ester thereof.

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$), and neopentyl (($CH_3)_3CCH_2$—).

"Alkenyl" refers to monovalent straight or branched hydrocarbyl groups having from 2 to 10 carbon atoms and preferably 2 to 6 carbon atoms or preferably 2 to 4 carbon atoms and having at least 1 and preferably from 1 to 2 sites of vinyl (>C=C<) unsaturation. Such groups are exemplified, for example, by vinyl, allyl, and but 3-en-1-yl. Included within this term are the cis and trans isomers or mixtures of these isomers.

"Alkynyl" refers to straight or branched monovalent hydrocarbyl groups having from 2 to 10 carbon atoms and preferably 2 to 6 carbon atoms or preferably 2 to 3 carbon atoms and having at least 1 and preferably from 1 to 2 sites of acetylenic (—C≡C—) unsaturation. Examples of such alkynyl groups include acetylenyl (—C≡CH), and propargyl (—CH$_2$C≡CH).

"Substituted alkyl" refers to an alkyl group having from 1 to 5, preferably 1 to 3, or more preferably 1 to 2 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, substituted sulfonyloxy, thioacyl, thiol, alkylthio, and substituted alkylthio, wherein said substituents are as defined herein.

"Heteroalkyl" refers to an alkyl group one or more carbons is replaced with —O—, —S—, SO$_2$, a P containing moiety as provided herein, —NR$^Q$—,

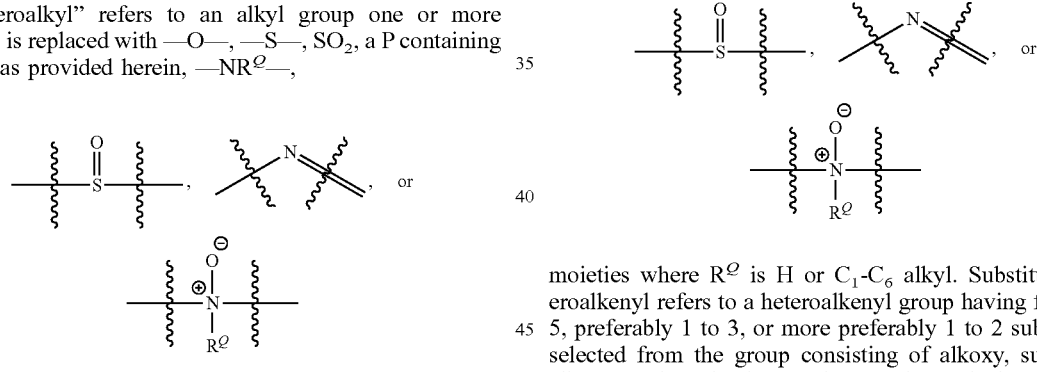

moieties where R$^Q$ is H or C$_1$-C$_6$ alkyl. Substituted heteroalkyl refers to a heteroalkyl group having from 1 to 5, preferably 1 to 3, or more preferably 1 to 2 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, substituted sulfonyloxy, thioacyl, thiol, alkylthio, and substituted alkylthio, wherein said substituents are as defined herein.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxyl, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, substituted sulfonyloxy, thioacyl, thiol, alkylthio, and substituted alkylthio, wherein said substituents are as defined herein and with the proviso that any hydroxyl or thiol substitution is not attached to a vinyl (unsaturated) carbon atom.

"Heteroalkenyl" refers to an alkenyl group one or more carbons is replaced with —O—, —S—, SO$_2$, a P containing moiety as provided herein, —NRQ-, moieties where R$^Q$ is H or C$_1$-C$_6$ alkyl. Substituted heteroalkenyl refers to a heteroalkenyl group having from 1 to 5, preferably 1 to 3, or more preferably 1 to 2 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, substituted sulfonyloxy, thioacyl, thiol, alkylthio, and substituted alkylthio, wherein said substituents are as defined herein.

"Substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, substituted sulfonyloxy, thioacyl, thiol, alkylthio, and substituted alkylthio, wherein said substituents are as defined herein and with the proviso that any hydroxyl or thiol substitution is not attached to an acetylenic carbon atom.

"Heteroalkynyl" refers to an alkynyl group one or more carbons is replaced with —O—, —S—, SO$_2$, a P containing moiety as provided herein, —NRQ-,

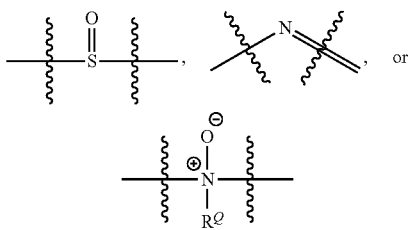

moieties where $R^Q$ is H or $C_1$-$C_6$ alkyl. Substituted heteroalkynyl refers to a heteroalkynyl group having from 1 to 5, preferably 1 to 3, or more preferably 1 to 2 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, substituted sulfonyloxy, thioacyl, thiol, alkylthio, and substituted alkylthio, wherein said substituents are as defined herein.

"Alkylene" refers to divalent saturated aliphatic hydrocarbyl groups having from 1 to 10 carbon atoms, preferably having from 1 to 6 and more preferably 1 to 3 carbon atoms that are either straight chained or branched. This term is exemplified by groups such as methylene (—CH$_2$—), ethylene (—CH$_2$CH$_2$—), n-propylene (—CH$_2$CH$_2$CH$_2$—), iso-propylene (—CH$_2$CH(CH$_3$)— or —CH(CH$_3$)CH$_2$—), butylene (—CH$_2$CH$_2$CH$_2$CH$_2$—), isobutylene (—CH$_2$CH (CH$_3$—)CH$_2$—), sec-butylene (—CH$_2$CH$_2$(CH$_3$—)CH—), and the like. Similarly, "alkenylene" and "alkynylene" refer to an alkylene moiety containing respective 1 or 2 carbon carbon double bonds or a carbon carbon triple bond.

"Substituted alkylene" refers to an alkylene group having from 1 to 3 hydrogens replaced with substituents selected from the group consisting of alkyl, substituted alkyl, alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl ester, cycloalkyl, substituted cycloalkyl, heteroaryl, substituted heteroaryl, heterocyclic, substituted heterocyclic, and oxo wherein said substituents are defined herein. In some embodiments, the alkylene has 1 to 2 of the aforementioned groups, or having from 1-3 carbon atoms replaced with —O—, —S—, or —NRQ- moieties where $R^Q$ is H or $C_1$-$C_6$ alkyl. It is to be noted that when the alkylene is substituted by an oxo group, 2 hydrogens attached to the same carbon of the alkylene group are replaced by "=O". "Substituted alkenylene" and "substituted alkynylene" refer to alkenylene and substituted alkynylene moieties substituted with substituents as described for substituted alkylene.

"Alkynylene" refers to straight or branched divalent hydrocarbyl groups having from 2 to 10 carbon atoms and preferably 2 to 6 carbon atoms or preferably 2 to 3 carbon atoms and having at least 1 and preferably from 1 to 2 sites of acetylenic (—C≡C—) unsaturation. Examples of such alkynylene groups include C≡C— and CH$_2$C≡C—.

"Substituted alkynylene" refers to alkynylene groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, substituted sulfonyloxy, thioacyl, thiol, alkylthio, and substituted alkylthio, wherein said substituents are as defined herein and with the proviso that any hydroxyl or thiol substitution is not attached to an acetylenic carbon atom.

"Heteroalkylene" refers to an alkylene group wherein one or more carbons is replaced with —O—, —S—, SO$_2$, a P containing moiety as provided herein, —NR$^Q$—,

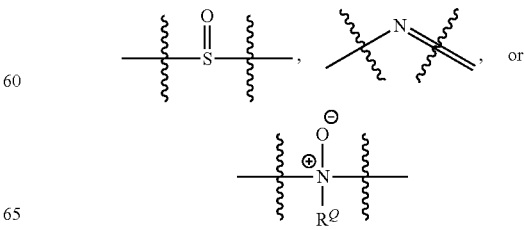

moieties where $R^Q$ is H or $C_1$-$C_6$ alkyl. "Substituted heteroalkylene" refers to heteroalkynylene groups having from 1 to 3 substituents, and preferably 1 to 2 substituents, selected from the substituents disclosed for substituted alkylene.

"Heteroalkenylene" refers to an alkenylene group wherein one or more carbons is replaced with —O—, —S—, $SO_2$, a P containing moiety as provided herein, —$NR^Q$—,

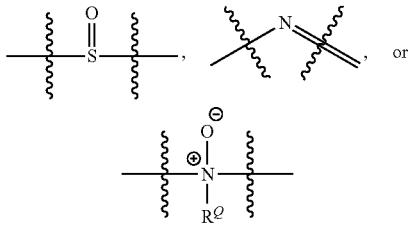

moieties where $R^Q$ is H or $C_1$-$C_6$ alkyl. "Substituted heteroalkenylene" refers to heteroalkynylene groups having from 1 to 3 substituents, and preferably 1 to 2 substituents, selected from the substituents disclosed for substituted alkenylene.

"Heteroalkynylene" refers to an alkynylene group wherein one or more carbons is replaced with —O—, —S—, $SO_2$, a P containing moiety as provided herein, —$NR^Q$—,

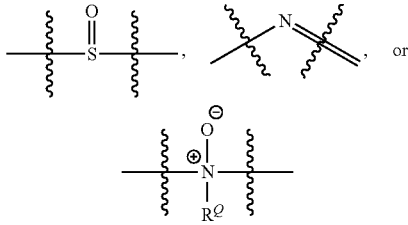

moieties where $R^Q$ is H or $C_1$-$C_6$ alkyl. "Substituted heteroalkynylene" refers to heteroalkynylene groups having from 1 to 3 substituents, and preferably 1 to 2 substituents, selected from the substituents disclosed for substituted alkynylene.

"Alkoxy" refers to the group O alkyl wherein alkyl is defined herein. Alkoxy includes, by way of example, methoxy, ethoxy, n propoxy, isopropoxy, n butoxy, t butoxy, sec butoxy, and n pentoxy.

"Substituted alkoxy" refers to the group O (substituted alkyl) wherein substituted alkyl is defined herein.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Acyl includes the "acetyl" group $CH_3C(O)$—.

"Acylamino" refers to the groups —$NR^{47}$C(O)alkyl, —$NR^{47}$C(O)substituted alkyl, —$NR^{47}$C(O)cycloalkyl, —$NR^{47}$C(O)substituted cycloalkyl, —$NR^{47}$C(O)cycloalkenyl, —$NR^{47}$C(O)substituted cycloalkenyl, —$NR^{47}$C(O)alkenyl, —$NR^{47}$C(O)substituted alkenyl, —$NR^{47}$C(O)alkynyl, —$NR^{47}$C(O)substituted alkynyl, —$NR^{47}$C(O)aryl, —$NR^{47}$C(O)substituted aryl, —$NR^{47}$C(O)heteroaryl, —$NR^{47}$C(O)substituted heteroaryl, —$NR^{47}$C(O)heterocyclic, and $NR^{47}$C(O)substituted heterocyclic wherein $R^{47}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, cycloalkenyl-C(O)O—, substituted cycloalkenyl-C(O)O—, heteroaryl-C(O)O—, substituted heteroaryl —C(O)O, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Amino" refers to the group $NH_2$.

"Substituted amino" refers to the group —$NR^{48}R^{49}$ where $R^{48}$ and $R^{49}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic, $SO_2$ a-lkyl, —$SO_2$-substituted alkyl, —$SO_2$-alkenyl, —$SO_2$-substituted alkenyl, —$SO_2$-cycloalkyl, —$SO_2$-substituted cycloalkyl, —$SO_2$-cycloalkenyl, —$SO_2$-substituted cylcoalkenyl, —$SO_2$-aryl, —$SO_2$-substituted aryl, —$SO_2$-heteroaryl, —$SO_2$-substituted heteroaryl, —$SO_2$-heterocyclic, and —$SO_2$-substituted heterocyclic and wherein $R^{48}$ and $R^{49}$ are optionally joined, together with the nitrogen bound thereto to form a heterocyclic or substituted heterocyclic group, provided that $R^{48}$ and $R^{49}$ are both not hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. When $R^{48}$ is hydrogen and $R^{49}$ is alkyl, the substituted amino group is sometimes referred to herein as alkylamino. When $R^{48}$ and $R^{49}$ are alkyl, the substituted amino group is sometimes referred to herein as dialkylamino. When referring to a monosubstituted amino, it is meant that either $R^{48}$ or $R^{49}$ is hydrogen but not both. When referring to a disubstituted amino, it is meant that neither $R^{48}$ nor $R^{49}$ are hydrogen.

"Aminocarbonyl" refers to the group —C(O)$NR^{50}R^{51}$ where $R^{50}$ and $R^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{50}$ and $R^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminothiocarbonyl" refers to the group —C(S)NR$^{50}$R$^{51}$ where R$^{50}$ and R$^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{50}$ and R$^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonylamino" refers to the group —NR$^{47}$C(O) NR$^{50}$R$^{51}$ where R$^{47}$ is hydrogen or alkyl and R$^{50}$ and R$^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic, and where R$^{50}$ and R$^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminothiocarbonylamino" refers to the group —NR$^{47}$C(S)NR$^{50}$R$^{51}$ where R$^{47}$ is hydrogen or alkyl and R$^{50}$ and R$^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{50}$ and R$^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonyloxy" refers to the group —O—C(O)NR$^{50}$R$^{51}$ where R$^{50}$ and R$^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{50}$ and R$^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminosulfonyl" refers to the group —SO$_2$NR$^{50}$R$^{51}$ where R$^{50}$ and R$^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{50}$ and R$^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminosulfonyloxy" refers to the group —O—SO$_2$NR$^{50}$R$^{51}$ where R$^{50}$ and R$^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{50}$ and R$^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminosulfonylamino" refers to the group —NR$^{47}$SO$_2$NR$^{50}$R$^{51}$ where R$^{47}$ is hydrogen or alkyl and R$^{50}$ and R$^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{50}$ and R$^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Amidino" refers to the group —C(=NR$^{52}$)NR$^{50}$R$^{51}$ where R$^{50}$, R$^{51}$, and R$^{52}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{50}$ and R$^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2 benzoxazolinone, 2H 1,4 benzoxazin 3(4H) one 7 yl, and the like) provided that the point of attachment is at an aromatic carbon atom. Preferred aryl groups include phenyl and naphthyl.

"Substituted aryl" refers to aryl groups which are substituted with 1 to 5, preferably 1 to 3, or more preferably 1 to 2 substituents selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, substituted sulfonyloxy, thioacyl, thiol, alkylthio, and substituted alkylthio, wherein said substituents are as defined herein.

"Arylene" refers to a divalent aromatic carbocyclic group of from 6 to 14 carbon atoms having a single ring or multiple condensed rings. "Substituted arylene" refers to an arylene having from 1 to 5, preferably 1 to 3, or more preferably 1 to 2 substituents as defined for aryl groups.

"Heteroarylene" refers to a divalent aromatic group of from 1 to 10 carbon atoms and 1 to 4 heteroatoms selected from the group consisting of oxygen, nitrogen and sulfur within the ring. "Substituted heteroarylene" refers to heteroarylene groups that are substituted with from 1 to 5, preferably 1 to 3, or more preferably 1 to 2 substituents selected from the group consisting of the same group of substituents defined for substituted aryl.

"Aryloxy" refers to the group —O-aryl, where aryl is as defined herein, that includes, by way of example, phenoxy and naphthoxy.

"Substituted aryloxy" refers to the group —O-(substituted aryl) where substituted aryl is as defined herein.

"Arylthio" refers to the group —S-aryl, where aryl is as defined herein.

"Substituted arylthio" refers to the group S (substituted aryl), where substituted aryl is as defined herein.

"Carbonyl" refers to the divalent group —C(O)— which is equivalent to —C(=O)—.

"Carboxyl" or "carboxy" refers to COOH or salts thereof.

"Carboxyl ester" or "carboxy ester" refers to the group —C(O)(O)-alkyl, —C(O)(O)-substituted alkyl, —C(O)O-alkenyl, —C(O)(O)-substituted alkenyl, —C(O)(O)-alkynyl, —C(O)(O)-substituted alkynyl, —C(O)(O)-aryl, —C(O)(O)-substituted-aryl, —C(O)(O)-cycloalkyl, —C(O)(O)-substituted cycloalkyl, —C(O)(O)-cycloalkenyl, —C(O)(O)-substituted cycloalkenyl, —C(O)(O)-heteroaryl, —C(O)(O)-substituted heteroaryl, —C(O)(O)-heterocyclic, and —C(O)(O)-substituted heterocyclic wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)amino refers to the group —NR$^{47}$C(O)(O)-alkyl, —NR$^{47}$C(O)(O)-substituted alkyl, —NR$^{47}$C(O)O-alkenyl, —NR$^{47}$C(O)(O)-substituted alkenyl, —NR$^{47}$C(O)(O)-alkynyl, —NR$^{47}$C(O)(O)-substituted alkynyl, —NR$^{47}$C(O)(O)-aryl, —NR$^{47}$C(O)(O)-substituted-aryl, —NR$^{47}$C(O)(O)-cycloalkyl, —NR$^{47}$C(O)(O)-substituted cycloalkyl, —NR$^{47}$C(O)(O)-cycloalkenyl, —NR$^{47}$C(O)(O)-substituted cycloalkenyl, —NR$^{47}$C(O)(O)-heteroaryl, —NR$^{47}$C(O)(O)-substituted heteroaryl, —NR$^{47}$C(O)(O)-heterocyclic, and —NR$^{47}$C(O)(O)-substituted heterocyclic wherein R$^{47}$ is alkyl or hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" refers to the group —O—C(O)O-alkyl, —O—C(O)O-substituted alkyl, —O—C(O)O-alkenyl, —O—C(O)O-substituted alkenyl, —O—C(O)O-alkynyl, —O—C(O)(O)-substituted alkynyl, —O—C(O)O-aryl, —O—C(O)O-substituted-aryl, —O—C(O)O-cycloalkyl, —O—C(O)O— substituted cycloalkyl, —O—C(O)O-cycloalkenyl, —O—C(O)O-substituted cycloalkenyl, —O—C(O)O-heteroaryl, —O—C(O)O-substituted heteroaryl, —O—C(O)O-heterocyclic, and —O—C(O)O— substituted heterocyclic wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" refers to the group CN.

"Cycloalkyl" refers to cyclic alkyl groups of from 3 to 10 carbon atoms having single or multiple cyclic rings including fused, bridged, and spiro ring systems. The fused ring can be an aryl ring provided that the non aryl part is joined to the rest of the molecule. Examples of suitable cycloalkyl groups include, for instance, adamantyl, cyclopropyl, cyclobutyl, cyclopentyl, and cyclooctyl.

"Cycloalkenyl" refers to non aromatic cyclic alkyl groups of from 3 to 10 carbon atoms having single or multiple cyclic rings and having at least one >C=C<ring unsaturation and preferably from 1 to 2 sites of >C=C<ring unsaturation.

"Substituted cycloalkyl" and "substituted cycloalkenyl" refers to a cycloalkyl or cycloalkenyl group having from 1 to 5 or preferably 1 to 3 substituents selected from the group consisting of oxo, thioxo, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, substituted sulfonyloxy, thioacyl, thiol, alkylthio, and substituted alkylthio, wherein said substituents are as defined herein.

"Cyclopropano" refers to:

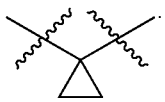 [SMILES: *C1(*)CC1]

"Cyclobutano" refers to:

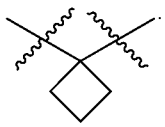 [SMILES: *C1(*)CCC1]

"Cycloalkyloxy" refers to —O-cycloalkyl.

"Substituted cycloalkyloxy refers to —O-(substituted cycloalkyl).

"Cycloalkylthio" refers to —S-cycloalkyl.

"Substituted cycloalkylthio" refers to —S-(substituted cycloalkyl).

"Cycloalkenyloxy" refers to —O-cycloalkenyl.

"Substituted cycloalkenyloxy" refers to —O-(substituted cycloalkenyl).

"Cycloalkenylthio" refers to —S-cycloalkenyl.

"Substituted cycloalkenylthio" refers to —S-(substituted cycloalkenyl).

"Guanidino" refers to the group —NHC(=NH)NH$_2$.

"Substituted guanidino" refers to —NR$^{53}$C(=NR$^{53}$)N(R$^{53}$)$_2$ where each R$^{53}$ is independently selected from the group consisting of hydrogen, alkyl, substituted alkyl, aryl, substituted aryl, heteroaryl, substituted heteroaryl, cycloalkyl, substituted cycloalkyl, heterocyclic, and substituted heterocyclic and two R$^{53}$ groups attached to a common guanidino nitrogen atom are optionally joined together with the nitrogen bound thereto to form a heterocyclic or substituted heterocyclic group, provided that at least one R$^{53}$ is not hydrogen, and wherein said substituents are as defined herein.

"Halo" or "halogen" refers to fluoro, chloro, bromo and iodo.

"Hydroxy" or "hydroxyl" refers to the group —OH.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N oxide (N→O), sulfinyl, or sulfonyl moieties. Certain non-limiting examples include pyridinyl, pyrrolyl, indolyl, thiophenyl, oxazolyl, thizolyl, and furanyl.

"Substituted heteroaryl" refers to heteroaryl groups that are substituted with from 1 to 5, preferably 1 to 3, or more preferably 1 to 2 substituents selected from the group consisting of the same group of substituents defined for substituted aryl.

"Heteroaryloxy" refers to —O-heteroaryl.

"Substituted heteroaryloxy" refers to the group —O-(substituted heteroaryl).

"Heteroarylthio" refers to the group —S-heteroaryl.

"Substituted heteroarylthio" refers to the group —S-(substituted heteroaryl).

"Heterocycle" or "heterocyclic" or "heterocycloalkyl" or "heterocyclyl" refers to a saturated or partially saturated, but not aromatic, group having from 1 to 10 ring carbon atoms and from 1 to 4 ring heteroatoms selected from the group consisting of nitrogen, sulfur, or oxygen. Heterocycle encompasses single ring or multiple condensed rings, including fused bridged and spiro ring systems. In fused ring systems, one or more of the rings can be cycloalkyl, aryl, or heteroaryl provided that the point of attachment is through a non-aromatic ring. In one embodiment, the nitrogen and/or sulfur atom(s) of the heterocyclic group are optionally oxidized to provide for the N oxide, sulfinyl, or sulfonyl moieties.

"Substituted heterocyclic" or "substituted heterocycloalkyl" or "substituted heterocyclyl" refers to heterocyclyl groups that are substituted with from 1 to 5 or preferably 1 to 3 of the same substituents as defined for substituted cycloalkyl.

"Heterocyclyloxy" refers to the group —O-heterocycyl.

"Substituted heterocyclyloxy" refers to the group —O-(substituted heterocycyl).

"Heterocyclylthio" refers to the group —S-heterocycyl.

"Substituted heterocyclylthio" refers to the group —S-(substituted heterocycyl).

Examples of heterocycle and heteroaryls include, but are not limited to, azetidine, pyrrole, furan, thiophene, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4 tetrahydroisoquinoline, 4,5,6,7 tetrahydrobenzo[b]thiophene, thiazole, thiazolidine, thiophene, benzo[b]thiophene, morpholinyl, thiomorpholinyl (also referred to as thiamorpholinyl), 1,1 dioxothiomorpholinyl, piperidinyl, pyrrolidine, and tetrahydrofuranyl.

"Nitro" refers to the group —NO$_2$.

"Oxo" refers to the atom (=O).

Phenylene refers to a divalent aryl ring, where the ring contains 6 carbon atoms.

Substituted phenylene refers to phenylenes which are substituted with 1 to 4, preferably 1 to 3, or more preferably 1 to 2 substituents selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, substituted sulfonyloxy, thioacyl, thiol, alkylthio, and substituted alkylthio, wherein said substituents are as defined herein.

"Spirocycloalkyl" and "spiro ring systems" refers to divalent cyclic groups from 3 to 10 carbon atoms having a cycloalkyl or heterocycloalkyl ring with a spiro union (the union formed by a single atom which is the only common member of the rings) as exemplified by the following structure:

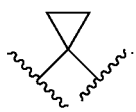 [SMILES: *C1(*)CC1]

"Sulfonyl" refers to the divalent group —S(O)$_2$—.

"Substituted sulfonyl" refers to the group —SO$_2$-alkyl, —SO$_2$-substituted alkyl, —SO$_2$-alkenyl, —SO$_2$-substituted alkenyl, SO$_2$-cycloalkyl, —SO$_2$-substituted cycloalkyl, —SO$_2$-cycloalkenyl, —SO$_2$-substituted cylcoalkenyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Substituted sulfonyl includes groups such as methyl —SO$_2$—, phenyl —SO$_2$—, and 4-methylphenyl-SO$_2$—.

"Substituted sulfonyloxy" refers to the group —OSO$_2$-alkyl, —OSO$_2$-substituted alkyl, —OSO$_2$-alkenyl, —OSO$_2$-substituted alkenyl, OSO$_2$-cycloalkyl, —OSO$_2$-substituted cycloalkyl, —OSO$_2$-cycloalkenyl, —OSO$_2$-substituted cylcoalkenyl, —OSO$_2$-aryl, —OSO$_2$-substituted aryl, —OSO$_2$-heteroaryl, —OSO$_2$-substituted heteroaryl, —OSO$_2$-heterocyclic, —OSO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Thioacyl" refers to the groups H—C(S)—, alkyl-C(S)—, substituted alkyl-C(S)—, alkenyl-C(S)—, substituted alkenyl-C(S)—, alkynyl-C(S)—, substituted alkynyl-C(S)—, cycloalkyl-C(S)—, substituted cycloalkyl-C(S)—, cycloalkenyl-C(S)—, substituted cycloalkenyl-C(S)—, aryl-C(S)—, substituted aryl-C(S)—, heteroaryl-C(S)—, substituted heteroaryl-C(S)—, heterocyclic-C(S)—, and substituted heterocyclic-C(S)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Thiol" refers to the group SH.

"Thiocarbonyl" refers to the divalent group —C(S)— which is equivalent to —C(=S)—.

"Thioxo" refers to the atom (=S).

"Alkylthio" refers to the group S-alkyl wherein alkyl is as defined herein.

"Substituted alkylthio" refers to the group —S-(substituted alkyl) wherein substituted alkyl is as defined herein.

A substituted ring can be substituted with one or more fused and/or spiro cycles. Such fused cycles include a fused cycloalkyl, a fused heterocyclyl, a fused aryl, a fused heteroaryl ring, each of which rings can be unsubstituted or substituted. Such spiro cycles include a fused cycloalkyl and a fused heterocyclyl, each of which rings can be unsubstituted or substituted.

It is understood that the above definitions are not intended to include impermissible substitution patterns (e.g., methyl substituted with 5 fluoro groups). Such impermissible substitution patterns are well known to the skilled artisan.

It is understood that the above definitions are not intended to include impermissible substitution patterns (e.g., methyl substituted with 5 fluoro groups). Such impermissible substitution patterns are well known to the skilled artisan.

"Pharmaceutically acceptable salt" refers to salts of a compound, which salts are suitable for pharmaceutical use and are derived from a variety of organic and inorganic counter ions well known in the art and include, when the compound contains an acidic functionality, by way of example only, sodium, potassium, calcium, magnesium, ammonium, and tetraalkylammonium; and when the molecule contains a basic functionality, salts of organic or inorganic acids, such as hydrochloride, hydrobromide, tartrate, mesylate, acetate, maleate, and oxalate (see Stahl and Wermuth, eds., "Handbook of Pharmaceutically Acceptable Salts," (2002), Verlag Helvetica Chimica Acta, Zurich, Switzerland), for a discussion of pharmaceutical salts, their selection, preparation, and use.

"Pulmonary hypertension" refers to all forms of pulmonary hypertension, WHO Groups 1-5. Pulmonary arterial hypertension, also referred to as PAH, refers to WHO Group 1 pulmonary hypertension. PAH includes idiopathic, heritable, drug- or toxin-induced, and persistent pulmonary hypertension of the newborn (PPHN).

Generally, pharmaceutically acceptable salts are those salts that retain substantially one or more of the desired pharmacological activities of the parent compound and which are suitable for in vivo administration. Pharmaceutically acceptable salts include acid addition salts formed with inorganic acids or organic acids. Inorganic acids suitable for forming pharmaceutically acceptable acid addition salts include, by way of example and not limitation, hydrohalide acids (e.g., hydrochloric acid, hydrobromic acid, hydroiodic acid, etc.), sulfuric acid, nitric acid, phosphoric acid, and the like.

Organic acids suitable for forming pharmaceutically acceptable acid addition salts include, by way of example and not limitation, acetic acid, trifluoroacetic acid, propionic acid, hexanoic acid, cyclopentanepropionic acid, glycolic acid, oxalic acid, pyruvic acid, lactic acid, malonic acid, succinic acid, malic acid, maleic acid, fumaric acid, tartaric acid, citric acid, palmitic acid, benzoic acid, 3-(4-hydroxybenzoyl) benzoic acid, cinnamic acid, mandelic acid, alkylsulfonic acids (e.g., methanesulfonic acid, ethanesulfonic acid, 1,2-ethane-disulfonic acid, 2-hydroxyethanesulfonic acid, etc.), arylsulfonic acids (e.g., benzenesulfonic acid, 4 chlorobenzenesulfonic acid, 2-naphthalenesulfonic acid, 4-toluenesulfonic acid, camphorsulfonic acid, etc.), glutamic acid, hydroxynaphthoic acid, salicylic acid, stearic acid, muconic acid, and the like.

Pharmaceutically acceptable salts also include salts formed when an acidic proton present in the parent compound is either replaced by a metal ion (e.g., an alkali metal ion, an alkaline earth metal ion, or an aluminum ion); by an ammonium ion (e.g., an ammonium ion derived from an organic base, such as, ethanolamine, diethanolamine, triethanolamine, morpholine, piperidine, dimethylamine, diethylamine, triethylamine, and ammonia); and an amino acid residue, i.e. a residue of an amino acid, such as lysine, arginine, etc.

Treprostinil, the active ingredient in Remodulin© (treprostinil) Injection, Tyvaso© (treprostinil) Inhalation Solution, and Orenitram© (treprostinil) Extended Release Tablets, was described in U.S. Pat. No. 4,306,075. Methods of making treprostinil and other prostacyclin derivatives are described, for example, in Moriarty, et al., *J. Org. Chem.* 2004, 69, 1890-1902, *Drug of the Future*, 2001, 26(4), 364-374, U.S. Pat. Nos. 6,441,245, 6,528,688, 6,700,025, 6,809,223, 6,756,117, 8,461,393, 8,481,782; 8,242,305, 8,497,393, 8,940,930, 9,029,607, 9,156,786 and 9,388,154 9,346,738; U.S. Published Patent Applications Nos. 2012-0197041, 2013-0331593, 2014-0024856, 2015-0299091, 2015-0376106, 2016-0107973, 2015-0315114, 2016-0152548, and 2016-0175319; PCT Application Publications No. WO2016/0055819 and WO2016/081658.

Various uses and/or various forms of treprostinil are disclosed, for example, in U.S. Pat. Nos. 5,153,222, 5,234, 953, 6,521,212, 6,756,033, 6,803,386, 7,199,157, 6,054,486, 7,417,070, 7,384,978, 7,879,909, 8,563,614, 8,252,839, 8,536,363, 8,410,169, 8,232,316, 8,609,728, 8,350,079, 8,349,892, 7,999,007, 8,658,694, 8,653,137, 9,029,607, 8,765,813, 9,050,311, 9,199,908, 9,278,901, 8,747,897, 9,358,240, 9,339,507, 9,255,064, 9,278,902, 9,278,903, 9,758,465; 9,422,223; 9,878,972; 9,624,156; U.S. Published Patent Applications Nos. 2009-0036465, 2008-0200449, 2008-0280986, 2009-0124697, 2014-0275616, 2014-0275262, 2013-0184295, 2014-0323567, 2016-0030371, 2016-0051505, 2016-0030355, 2016-0143868, 2015-0328232, 2015-0148414, 2016-0045470, 2016-0129087, 2017-0095432; 2018-0153847 and PCT Application Publications Nos. WO00/57701, WO20160105538, WO2016038532, WO2018/058124.

Treprostinil has the following chemical formula:

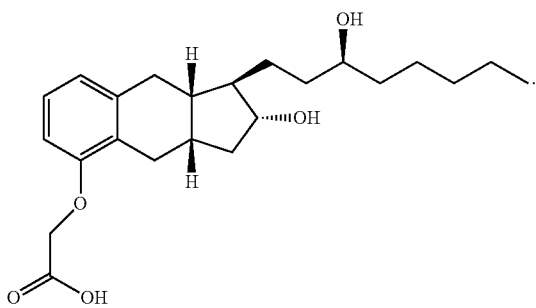

Treprostinil molecule has two hydroxyl groups: one on the cyclopentyl ring and one on the alkyl chain as well as one carboxyl group. These reactive groups of treprostinil molecules may lead to formation of impurities in treprostinil formulations. For example, the carboxyl group on one treprostinil molecule may react with one of the hydroxyl groups on another treprostinil molecule, thereby, forming a dimer. The reactive groups on treprostinil molecules may also form undesirable impurities when reacting with other ingredients in a treprostinil formulation. For example, when a treprostinil formulation contains a carboxyl group containing ingredient, such as (E)-3,6-bis[4-(N-carbonyl-2-propenyl)amidobutyl]-2,5-diketopiperazine (FDKP) in a dry powder inhalation treprostinil formulation, the carboxyl group of such ingredient may react with one of the hydroxyl groups on a treprostinil molecule, thereby forming an undesirable impurity. The carboxyl group on a treprostinil molecule may also react to a hydroxyl group of a hydroxyl group containing ingredient, such as an alcohol, e.g. methanol or ethanol, resulting in a formation of an undesirable impurity.

Figure 2:
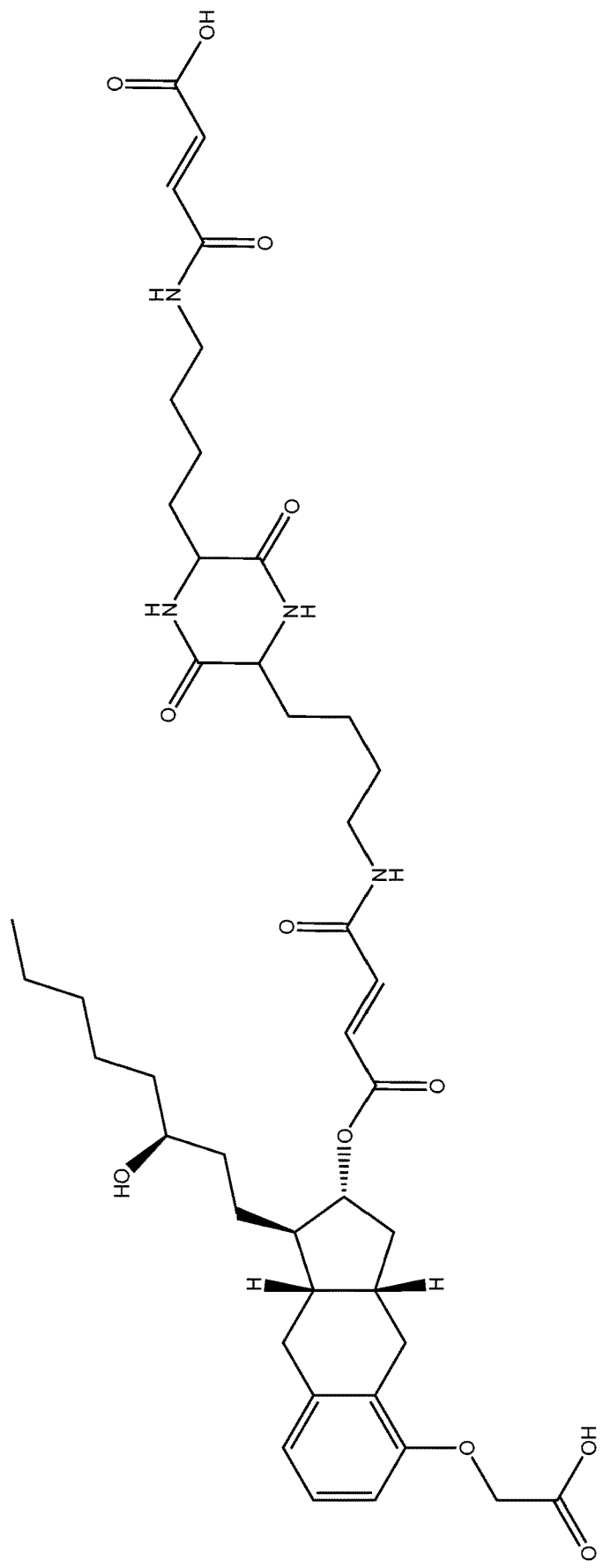
FIG. 2 shows an impurity, which may be via a reaction between a hydroxyl group on cyclopentyl ring of a treprostinil molecule and FDKP.
Figure 3:
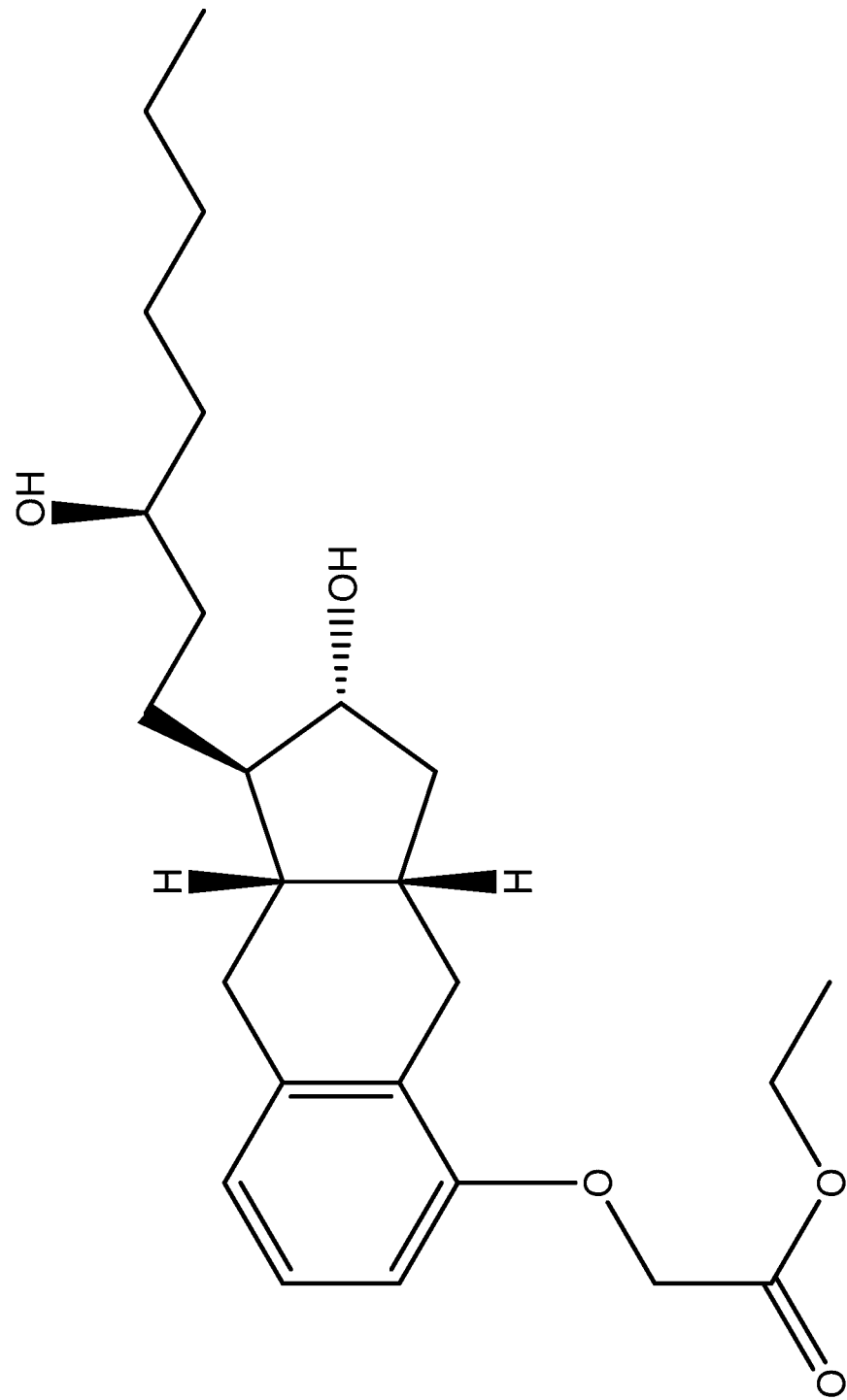
FIG. 3 shows an impurity, which may be formed via a reaction between a carboxyl group of a treprostinil molecule and a hydroxyl group of ethanol.

WO2019/237028 discloses a dry powder composition comprising treprostinil and FDKP. In a preparation process, the dry powder composition is exposed to an alcohol, such as methanol or ethanol. FIG. 1-3 illustrate undesirable impurities, which may be formed due to (a) a reaction of the alkyl chain hydroxyl group of a treprostinil molecule with a carboxyl group of FDKP; (b) a reaction of the cyclopentyl ring hydroxyl group of a treprostinil molecule with a carboxyl group of FDKP; and (c) a reaction between the carboxyl group of a treprostinil with a hydroxyl group of ethanol. FIG. 4-5 each show a treprostinil dimer impurity, which may be formed via a intermolecular reaction between a carboxyl group of a treprostinil molecule and a hydroxyl group of another Treprostinil.

Treprostinil formulations, such a dry powder formulation comprising treprostinil and FDKP disclosed in WO2019/237028, are often stored at low temperatures, such as temperatures below a room temperature, in order to reduce a rate of formation of undesirable impurities.

An embodiment is a formulation comprising a salt or prodrug of treprostinil, which further includes a carboxy-group containing ingredient, e.g. FDKP, such as an FDKP-based powder formulation, which is preferably a dry powder formulation. The use of a treprostinil prodrug or a treprostinil salt instead of treprostinil as a free acid may reduce and/or eliminate one or more undesirable impurities.

In some embodiments, a formulation, which contains a carboxy-group containing ingredient, e.g., FDKP, such as an FDKP based dry powder formulation, may also comprise a pharmaceutically acceptable salt of treprostinil. For example, a salt of treprostinil may be a salt disclosed in one of the following documents, each of which is incorporated by reference in its entirety: PCT publication No. WO2005/007081; U.S. Pat. Nos. 7,417,070; 9,701,611; 9,988,334. Specific examples of treprostinil salts may include treprostinil diethanolamine; treprostinil tromethamine, treprostinil arginine; treprostinil lysine salt, treprostinil N-methylglucamine, treprostinil magnesium, treprostinil ammonium; treprostinil potassium, treprostinil calcium, treprostinil ethylenediamine, treprostinil choline, treprostinil tris(hydroxymethyl)aminomethane (treprostinil TRIS), treprostinil procaine, treprostinil benzathine, treprostinil sodium, as well as the lysine, arginine and potassium salts of treprostinil.

In some embodiments, a formulation, which contains a carboxy-group containing ingredient, e.g. FDKP, such as an FDKP based dry powder formulation, may also comprise a treprostinil prodrug or its pharmaceutically acceptable salt. For example, in some embodiments, the treprostinil prodrug may be a treprostinil prodrug disclosed in one of the following documents, each of which is incorporated by reference in its entirety: PCT publication No. WO2005/007081; U.S. Pat. Nos. 7,384,978, 7,417,070, 7,544,713, 8,252,839, 8,410,169, 8,536,363, 9,050,311, 9,199,908, 9,278,901, 9,422,223; 9,624,156, 9,878,972, 9,371,264, 9,394,227, 9,505,737, 9,643,911, 9,701,616, 9,776,982, 9,845,305, 9,957,200, 10,053,414, 10,246,403, 10,344,012, 10,450,290, 10,464,877, 10,464,878, 10,703,706, 10,752, 733, 9,255,064, 9,469,600, 10,010,518, 10,343,979, 10,526, 274; U.S. Patent Application Publications Nos. 2018-0153847, 2021-0054009; 2021-0378996; U.S. patent application Ser. No. 17/549,573 filed Dec. 13, 2021.

In some embodiments, the prodrug may have a carboxyl group of a corresponding unsubstituted treprostinil molecule, replaced with a moiety, which has a lower chemical reactivity than that of the carboxyl group of the unsubstituted treprostinil molecule.

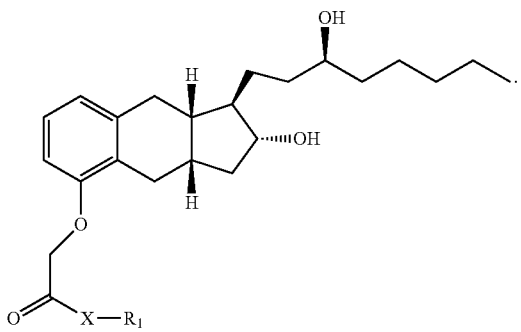

X=O; R$_1$ Alkyl such as CH$_3$; C$_2$H$_5$; Aryl; Substituted aryl; branched alkyl such as pivolyl, isopropyl etc.
X=N; R$_1$

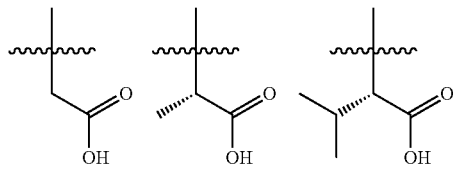

In some embodiments, the treprostinil prodrug may be a prodrug, which one of hydroxyl groups and a carboxyl group of a corresponding unsubstituted treprostinil molecule, each replaced with a moiety, which has a lower chemical reactivity than that of the respective group of the unsubstituted treprostinil molecule.

In some embodiments, the treprostinil prodrug may be a prodrug, which has each of three reactive groups of a corresponding unsubstituted treprostinil molecule, i.e. two hydroxyl groups and a carboxyl group, replaced with a moiety, which has a lower chemical reactivity than that of the respective reactive group of the unsubstituted treprostinil molecule.

For example, in some embodiments, the treprostinil prodrug may have the treprostinil prodrug has the following formula:

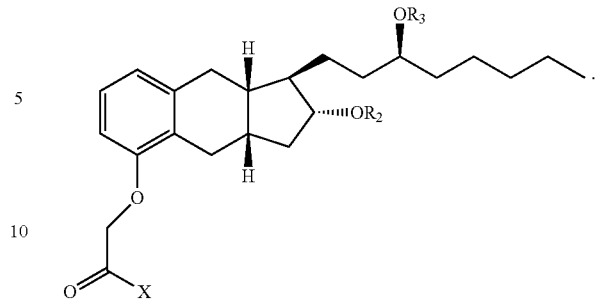

R$_2$ may be a first promoiety, R$_3$ may be a second promoiety; and X may be a salt moiety or a third promoeity. Each of OR$_2$ and OR$_3$ may have a lower chemical reactivity with a carboxyl group, such as a carboxyl group of a carboxyl group containing compound, such as FDKP, than that of the respective hydroxyl group of unsubstituted treprostinil. The C=OX group in the prodrug may have a lower chemical reactivity with a hydroxyl group, such a hydroxyl group of an alcohol, such as methanol or ethanol, than that of the carboxyl group (COOH) of unsubstituted treprostinil.

The treprostinil prodrug or the treprostinil salt may result in a lower amount of impuritie(s) in a treprostinil formulation, such as a treprostinil formulation containing a carboxylic group containing ingredient, such as FDKP, compared to a treprostinil formulation with unsubstituted treprostinil.

In some embodiments, the prodrug or the treprostinil salt may also allow using milder conditions for storing a treprostinil formulation, such as a dry powder formulation, which contains a carboxylic group containing ingredient, such as FDKP, compared to a treprostinil formulation with unsubstituted treprostinil. For example, in some embodiments, the treprostinil formulation, such as a dry powder formulation, which contains (a) the treprostinil prodrug or the treprostinil salt and (b) the carboxylic group containing ingredient, such as FDKP, may be stored at room temperature, such as 18° C. to 30° C. or 20° C. to 28° C. or 22° C. to 25° C. or any value or subrange within these ranges for at least a period of at least 3 months or at least 6 months or at least 12 months or a period from 3 months to 36 months or from 6 months to 30 months or from 12 to 18 months or any value or subrange within these ranges.

In some embodiments, the prodrug may be water soluble. Using water soluble prodrugs may allow avoiding the use of organic solvent(s), such as ethanol or methanol, and hence avoiding a formation of impurities due to reaction with the prodrug with the organic solvent(s).

In some embodiments, X may be a salt moiety, i.e. O$^-$·a salt counterion. In some embodiments, the salt counterion may be a counterion from an amino acid. In some embodiments, the amino acid may be a naturally occurring amino acid. In some embodiments, the amino acid may an L-isomer of a naturally occurring amino acid. Yet in some embodiments, the amino acid be a D-isomer of a naturally occurring amino acid. In some embodiments, the amino acid may be an amino acid selected from 20 standard amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine. In some embodiments, the amino acid salt moiety, such as for example, an arginine salt moiety, may produce a water soluble prodrug.

In some embodiments, X may be a third promoiety. For example, in some embodiments, X may be $OR_9$ or $NR_1R_6$; with $R_9$ being, for example alkyl chain $C_1$-$C_{20}$,

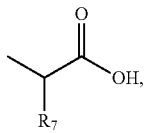

$R_1$ being H or $C_1$-$C_4$ alkyl, $R_6$ being

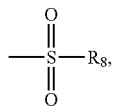

and $R_7$ and $R_8$ being independently H or $C_1$-$C_4$ alkyl.

In some embodiments, $R_2$ and $R_3$ may be independently selected from a phosphorous containing group, —C(O)$R^6$, or an -A-B—C substituent, wherein:
  A is optionally substituted $C_1$-$C_6$ alkylene, —$NR^6$—, —C(O)—, —C(O)O—, or —C(O)$NR^6$—;
  B is a bond, optionally substituted $C_1$-$C_6$ alkylene, —C(O)—, —O—, —S—, optionally substituted heterocyclyl; and
  C is optionally substituted heterocyclyl, optionally substituted heteroaryl, optionally substituted aryl, optionally substituted cycloalkyl, —(OCH$_2$CH$_2$)$_q$—$OR^6$, —C(O)N($R^6$)$_2$, —C(O)N($R^{18}$)$_2$, —C(O)$R^6$, —CO$_2$H, —$OR^6$, —N($R^{18}$)$_2$, —N($R^6$)$_2$, or

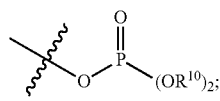

wherein:
  both $R^{18}$ together form an optionally substituted 3-8 membered heterocyclyl;
  each $R^6$ is independently H, optionally substituted $C_1$-$C_6$ alkyl, optionally substituted heteroaryl, optionally substituted aryl, or both of $R^6$ together form an 4 to 8 membered optionally substituted heterocyclyl or a 5 membered optionally substituted heteroaryl;
  or wherein the second promoiety and the third promoiety are joined together to form —C(O)—, —SO$_2$—,

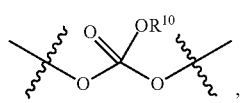

in an 8-12 membered heterocyclyl, wherein
  each $R^{10}$ is H, optionally substituted $C_1$-$C_6$ alkyl, optionally substituted $C_1$-$C_6$ alkenyl, optionally substituted cycloalkyl, optionally substituted heteroaryl, or optionally substituted aryl; and
  q is 0, 1, 2, 3, 4, 5 or 6.

In some embodiments, each of $R_2$ and $R_3$ may be independently selected from a phosphorous containing group or —C(O)$R^6$, and $R^6$ is optionally substituted $C_1$-$C_6$ alkyl.

In some embodiments, each of $R_2$ and $R_3$ are independently selected from CH$_2$OBn, CH$_2$OH,

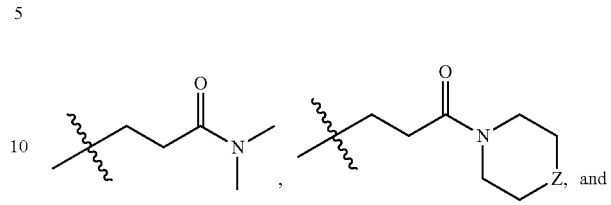

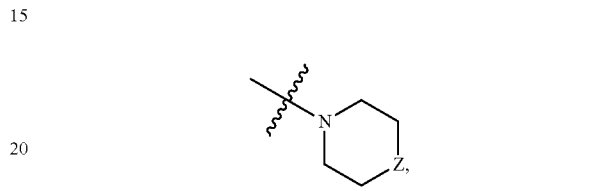

wherein Z is O or CH$_2$.

In some embodiments, $R_2$ and $R_3$ are each independently selected from $C_1$-$C_6$ alkyl, which may be linear or branched, and O—$R_{20}$, wherein $R_{20}$ is optionally substituted $C_1$-$C_6$ alkyl, such as linear or branched $C_1$-$C_6$ alkyl having one or more CH$_2$ groups optionally substituted with O.

In some embodiments, $R^2$ and $R^3$ may be the same chemical group. For example, in some embodiments, $R_2$ and $R_3$ may be each a phosphate group. In some embodiments, $R_2$ and $R_3$ may be each C(O)$R^6$ with $R^6$ being $C_1$-$C_6$ alkyl, such as methyl, ethyl, propyl, isopyl, n-butyl, sec-butyl, isobutyl or t-butyl. In some embodiments, $R_2$ and $R_3$ may be each $C_1$-$C_6$ alkyl, such as methyl, ethyl, propyl, isopropyl, n-butyl, t-butyl, sec-butyl or isobutyl. In some embodiments, $R_2$ and $R_3$ may be each O—$R_{20}$, such as OMe, OEt, O$^i$Pr or O(CH$_2$)$_2$OMe.

In some embodiments, $R_2$ and $R_3$ are joined together to form —C(O)—.

In some embodiments, the treprostinil prodrug or a salt of the treprostinil prodrug may have one of the following chemical formulas:

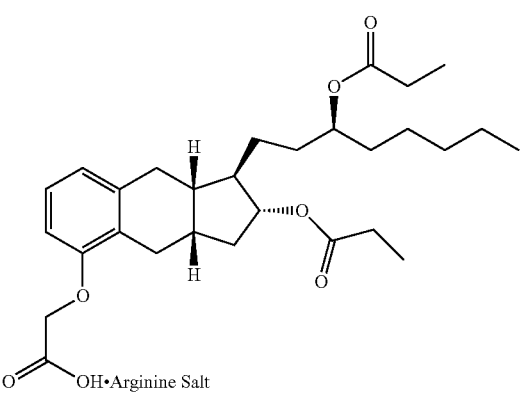

Water Soluble

23
-continued
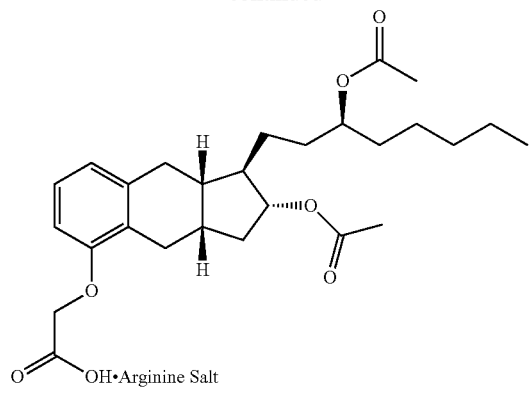
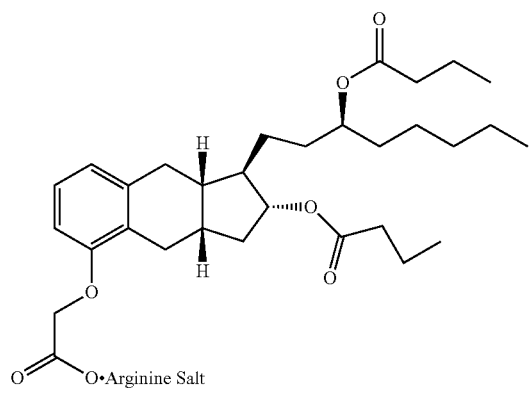
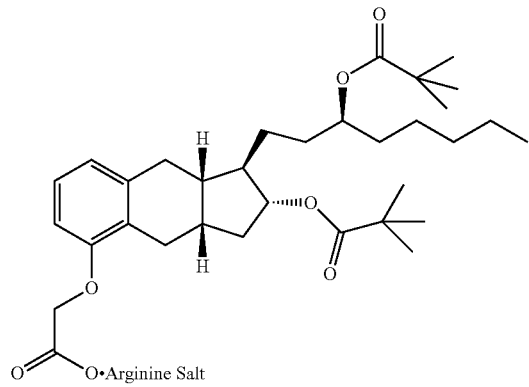
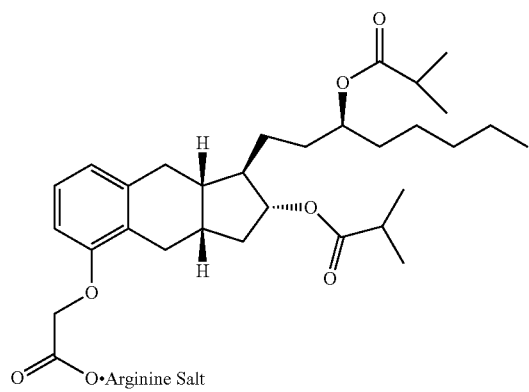
24
-continued
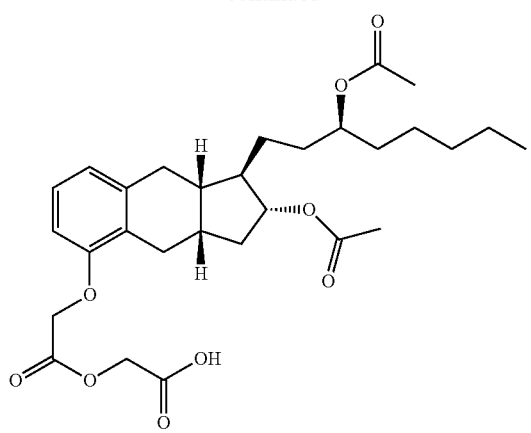
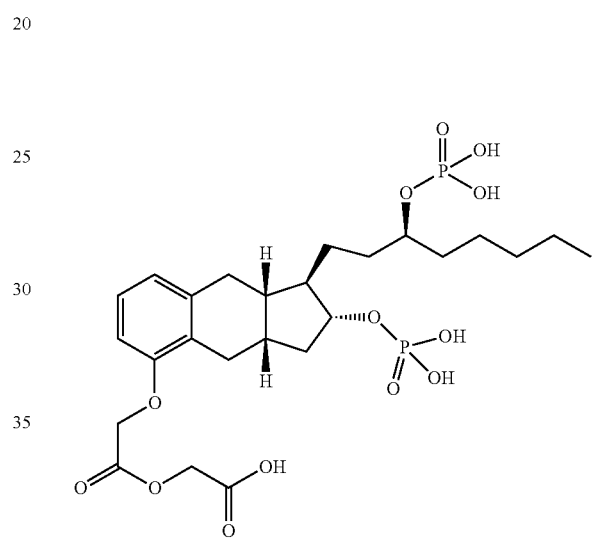
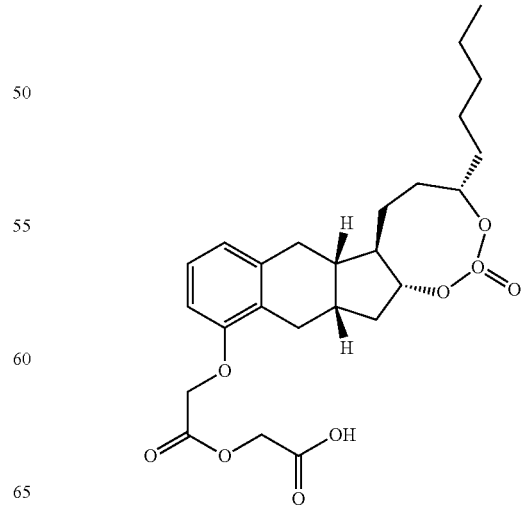

-continued

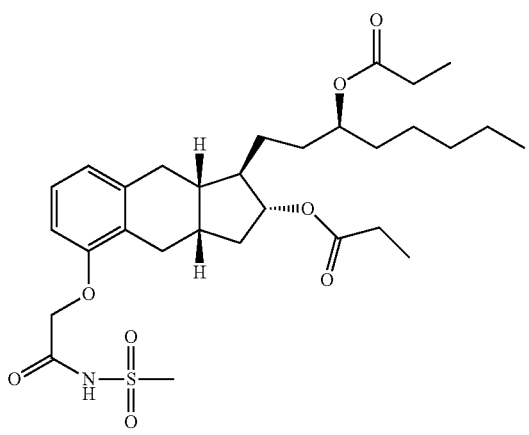

-continued

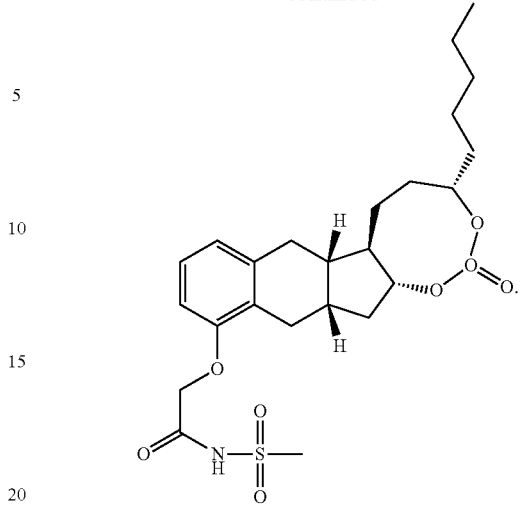

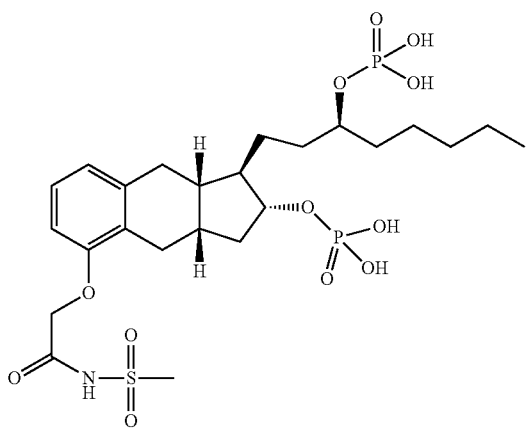

In some embodiments, the treprostinil prodrug or a salt of the treprostinil prodrug may be one or more of the following: Treprostinil Diacetate Potassium Salt; Treprostinil Dipropionate Potassium Salt; Treprostinil Dibutyrate Potassium Salt; Treprostinil Methyl Dicarbonate Potassium Salt; Treprostinil Diacetate L-Arginine Salt; Treprostinil Dipropionate L-Arginine Salt; Treprostinil Dibutyrate L-Arginine Salt; Treprostinil Methyl Dicarbonate L-Arginine Salt; Treprostinil Diacetate L-Lysine Salt; Treprostinil Dipropionate L-Lysine Salt; Treprostinil Dibutyrate L-Lysine Salt; Treprostinil Diisobutyrate L-Lysine Salt; Treprostinil Dipivalate L-Lysine Salt; Treprostinil Methyl Dicarbonate L-Lysine Salt; Treprostinil Ethyl Dicarbonate L-Lysine Salt; Treprostinil Isopropyl Dicarbonate L-Lysine Salt; Treprostinil bis(2-Methoxyethylcarbonate) L-Lysine Salt; Treprostinil Dihydroxyacetate L-Lysine Salt; Treprostinil bis(Dimethylsuccinamate) L-Lysine Salt; Treprostinil bis(Morpholinosuccinamate) L-Lysine Salt; Treprostinil bis(Piperidinylsuccinamate) L-Lysine Salt; Treprostinil Dimorpholinocarbamate L-Lysine Salt; and Treprostinil Dipiperidinylcarbamate L-Lysine Salt.

In some embodiments, the prodrugs may prepared by combining techniques from one or more U.S. patent application publications No. 2005-0085540 and 2018-0153847; U.S. Pat. No. 9,701,611; and U.S. patent application publication No. 2021-0054009, each of which is incorporated herein by reference in its entirely. For example, for the prodrugs having X being O⁻.arginine counterion while $R_2$ and $R_3$ being the same moiety selected from phosphate and —C(O)R⁶, a preparation technique may involve combining a synthesis of disubstituted prodrugs, such as prodrugs LXX-LXXIII in U.S. patent application publication No. 2021-0054009, with salt forming techniques of U.S. Pat. No. 9,701,611. For the prodrugs having X being $NR_1R_6$; $R_1$ being H, $R_6$ being

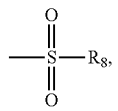

$R_8$ being independently H or $C_1$-$C_4$ alkyl, while $R_2$ and $R_3$ being the same moiety selected from phosphate and —C(O)R⁶, a preparation technique may involve combining a synthesis of disubstituted prodrugs, such as prodrugs LXX-LXXIII in U.S. patent application publication No. 2021-0054009, with a technique for synthesis of prodrug XIV in the same application. For the prodrugs having X being O$^-$.arginine counterion while $R_2$ and $R_3$ forming —C(O)—., a preparation technique may involve combining a synthesis of prodrug XXIV in U.S. patent application publication No. 2021-0054009, with salt forming techniques of U.S. Pat. No. 9,701,611. For the prodrugs having X being $NR_1R_6$; $R_1$ being H, $R_6$ being

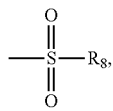

$R_8$ being independently H or $C_1$-$C_4$ alkyl, while $R_2$ and $R_3$ forming —C(O)—., a preparation technique may involve combining a synthesis of prodrug XXIV in U.S. patent application publication No. 2021-0054009, with a technique for synthesis of prodrug XIV in the same application. The prodrugs may be also synthesized as outlined in the Example below.

One or more of the prodrugs and/or salts may be used in an effective amount in a pharmaceutical composition or formulation, which may also include a carboxyl-group containing non-active ingredient such as FDKP. For example, the composition or formulation may be a dry powder formulation comprising one or more of the prodrugs and/or salts and a carboxyl-group containing non-active ingredient, such as FDKP.

The term "effective amount" may mean an amount of a treprostinil prodrug, a treprostil salt and/or a salt of a treprostinil prodrug, which may be necessary to treat the disease or condition. In some embodiments, an effective amount of treprostinil prodrug and/or salt may be the same or similar to an effective amount of treprostinil for treating the same disease or condition. In some embodiments, an effective amount of treprostinil prodrug and/or salt may be different from an effective amount of treprostinil for treating the same disease or condition. A person of ordinary skill in the art would be able to determine and "effective amount" of the treprostinil prodrug and/or salt based, for example, on the relevant disease or condition, the amount of treprostinil known to treat, ameliorate, or prevent the disease or condition, and the rate at which the prodrug and/or salt converts to treprostinil in vivo.

In some embodiments, a method of treating a disease or condition is provided, the method comprising administering to a subject, such as a human being, a compound (e.g. a prodrug and/or salt) or composition or formulation disclosed herein. In some embodiments, the disease or condition is one or more selected from the group consisting of pulmonary hypertension, congestive heart failure, peripheral vascular disease, Raynaud's phenomenon, Scleroderma, renal insufficiency, peripheral neuropathy, digital ulcers, intermittent claudication, ischemic limb disease, peripheral ischemic lesions, pulmonary fibrosis and asthma. In some embodiments, the disease is pulmonary hypertension.

In some embodiments, a formulation, such as an FDKP based dry powder formulation, which contains (a) a carboxy-group containing ingredient, e.g. FDKP, and (b) a treprostinil salt, a treprostinil prodrug or a salt of a treprostinil prodrug, may be administered by inhalation, such as oral inhalation or nasal inhalation. In some embodiments, the formulation may be administered using a dry powder inhaler.

Dry powder inhalers are disclosed, for example, in U.S. Pat. Nos. 7,305,986, 7,464,706, 8,499,757 and 8,636,001, PCT publication Wo2019237028, each of which is incorporated by reference.

In some embodiments, a dry powder inhaler may comprise a cartridge, which may be a replaceable cartridge, comprising an FDKP based dry powder formulation containing treprostinil prodrug and/or salt. In some embodiments, a dry powder inhaler may a breath-powered inhaler which may be compact, reusable or disposable. A dry powder inhaler may have a number of various shapes and sizes, and may comprise a system of airflow conduit pathways for the effective and rapid delivery of the powder medicament to the lungs and/or the systemic circulation.

Embodiments described herein are further illustrated by, though in no way limited to, the following working examples.

Example 1

Scheme 1: General Procedure for Synthesis of Treprostinil Di-substituted Prodrug Salts (4)

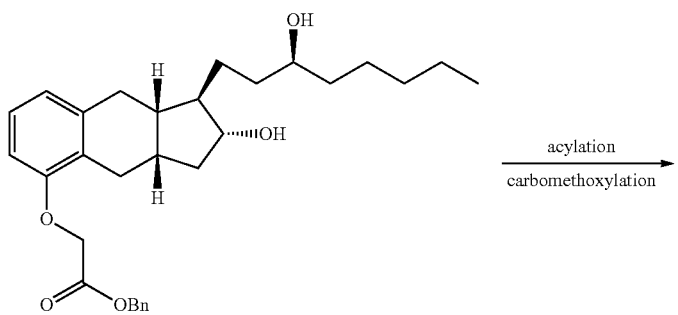

1

-continued
Scheme 1: General Procedure for Synthesis of Treprostinil Di-substituted Prodrug Salts (4)
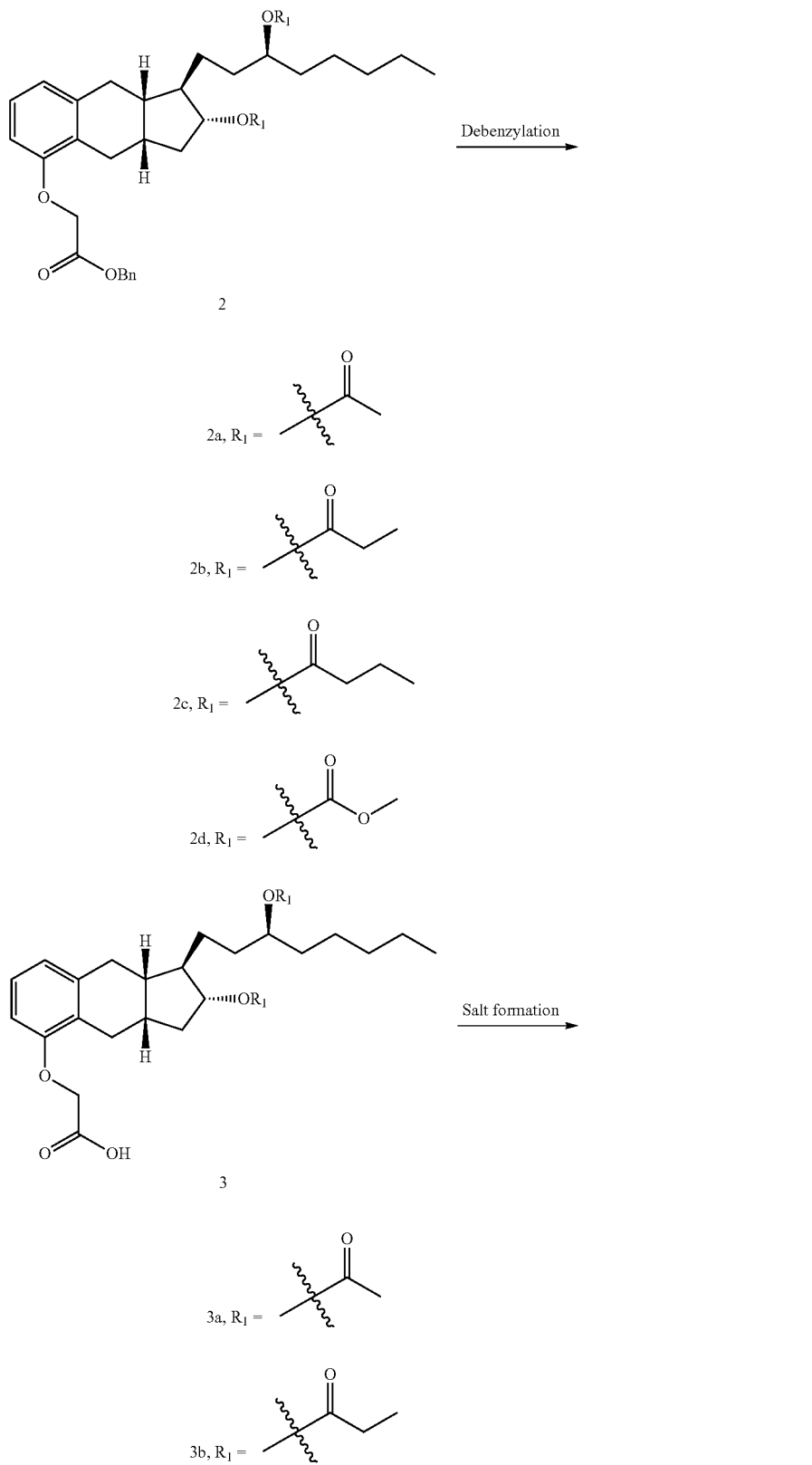

Scheme 1: General Procedure for Synthesis of Treprostinil Di-substituted Prodrug Salts (4)

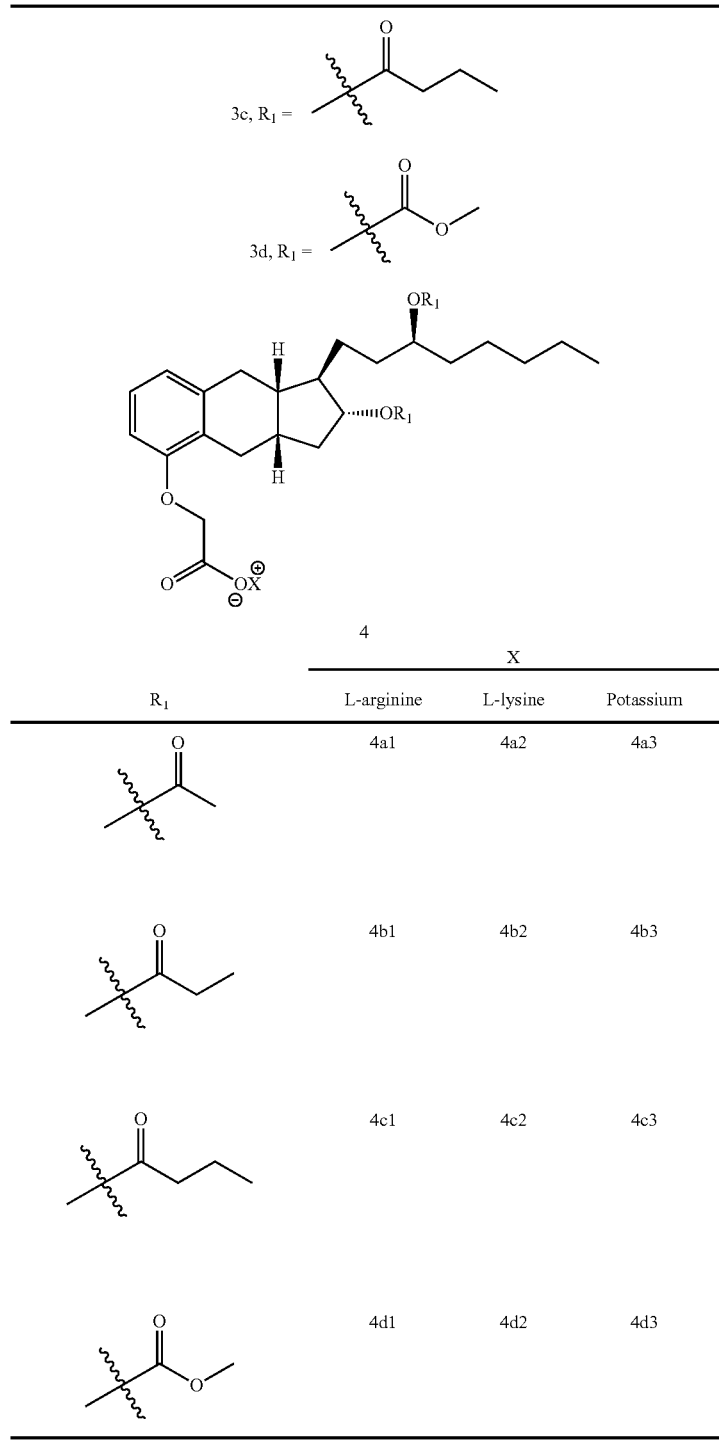

| R₁ | X | | |
|---|---|---|---|
| | L-arginine | L-lysine | Potassium |
| (acetyl) | 4a1 | 4a2 | 4a3 |
| (propanoyl) | 4b1 | 4b2 | 4b3 |
| (butanoyl) | 4c1 | 4c2 | 4c3 |
| (methyl carbonate) | 4d1 | 4d2 | 4d3 |

General Procedure for the Syntheses of Treprostinil Benzyl Ester Di-Substituted Prodrugs

Acylation and Carbomethoxylation

To a stirring solution of treprostinil benzyl ester (1) (1.0 eq.) and DMAP (2.0 eq) in dichloromethane (DCM) (20 v/wt) was added respective anhydride (1.5 eq) or methyl chloroformate (1.5 eq). The resulting mixture was stirred at room temperature for 1 h. The solvent was removed in vacuo to give crude product which was purified on silica gel column chromatography to give treprostinil benzyl ester diacetate (2a) or dipropionate (2b) or dibutanoate (2c) or dicarbonate (2d). These compounds (2a, 2b, 2c and 2d) were characterized by $^1$H NMR and LCMS.

General Procedure for the Syntheses of Treprostinil Di-Substituted Prodrugs (3a-d)

Debenzylation

To a solution of treprostinil benzyl ester di-substituted prodrugs (2a-d) (1.0 eq) in ethyl acetate (20 v/wt) (and 1 v/wt water) was added 5% palladium on carbon (~50% water) (10-25 wt %) under argon. The mixture was evacuated under house vacuum and replaced by hydrogen (filled in a balloon) at room temperature and this process was repeated two times. The reaction mixture was stirred under the atmosphere of hydrogen at room temperature for 1-3 h. The mixture was filtered through Celite pad and washed with EtOAc. The filtrate was evaporated in vacuo to give pure treprostinil di-substituted prodrugs (3a-d) The pure products were characterized by IR, $^1$H NMR, $^{13}$C NMR and LC-MS.

General Procedure for Salt Formation of Treprostinil Di-Substituted Prodrugs (4a-d)

The compounds (3a-d) were dissolved in acetone to obtain a clear solution and then the base is added as an aqueous solution. This was heated to ensure the salt formation. This mixture was evaporated and the solid was triturated with isopropyl acetate and heptane. This was evaporated to obtain salt as a free flowing powder. The salts (4a-d) were characterized by $^1$H NMR, $^{13}$C Nuclear Magnetic Resonance (NM/R), melting point (MIP) measurement, Liquid chromatography-mass spectrometry (LC-MS) and infrared (IR) spectroscopy.

| S. No | Name | Structure | Number | Salts | MP (° C.) |
|---|---|---|---|---|---|
| 1. | Treprostinil Diacetate | 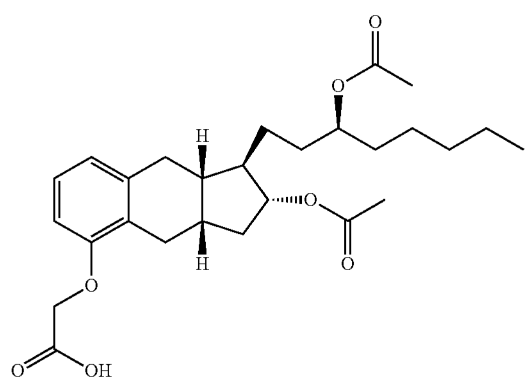 [SMILES: CCCCC[C@@H](CC[C@@H]1[C@H]2Cc3cccc(OCC(=O)O)c3C[C@H]2C[C@H]1OC(C)=O)OC(C)=O] | 4a1 | Arginine | 136-139 |
| | | | 4a2 | Lysine | 167-171 |
| | | | 4a3 | Potassium | 228-232 |
| 2. | Treprostinil Dipropionate | 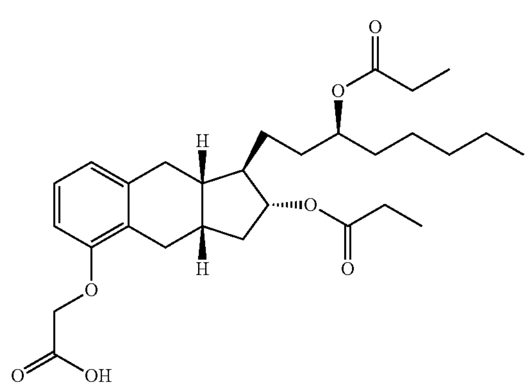 [SMILES: CCCCC[C@@H](CC[C@@H]1[C@H]2Cc3cccc(OCC(=O)O)c3C[C@H]2C[C@H]1OC(=O)CC)OC(=O)CC] | 4b1 | Arginine | 210-213 |
| | | | 4b2 | Lysine | 179-182 |
| | | | 4b3 | Potassium | 230-233 |

-continued
| S. No | Name | Structure | Number | Salts | MP (° C.) |
|---|---|---|---|---|---|
| 3. | Treprostinil Dicarbonate | 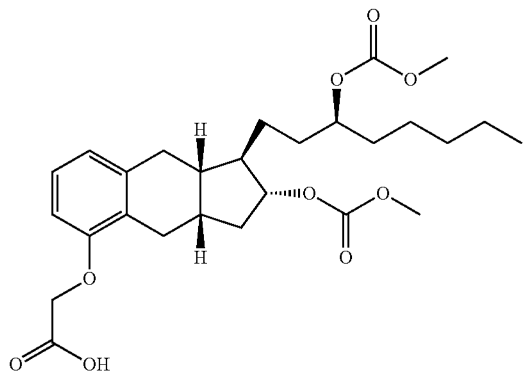 [SMILES: CCCCC[C@@H](CC[C@@H]1[C@H]2Cc3cccc(OCC(=O)O)c3C[C@H]2C[C@H]1OC(=O)OC)OC(=O)OC] | 4c1 | Arginine | 184-186 |
| | | | 4c2 | Lysine | 173-176 |
| | | | 4c3 | Potassium | 196-198 |
| 4. | Treprostinil Dibutanoate | 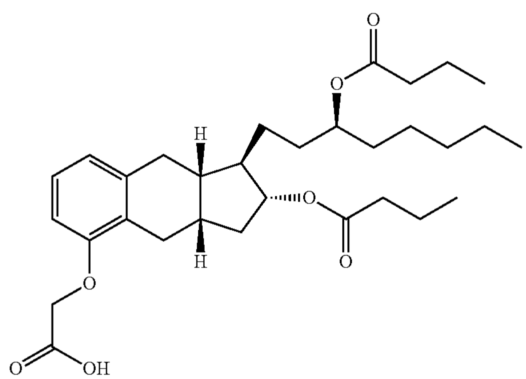 [SMILES: CCCCC[C@@H](CC[C@@H]1[C@H]2Cc3cccc(OCC(=O)O)c3C[C@H]2C[C@H]1OC(=O)CCC)OC(=O)CCC] | 4d1 | Arginine | 194-196 |
| | | | 4d2 | Lysine | 178-181 |
| | | | 4d3 | Potassium | 214-219 |
Synthesis of Treprostinil Acetoxy Acetate Acid (7)
Scheme 2: Synthesis of Treprostinil Acetoxy Acetate Acid
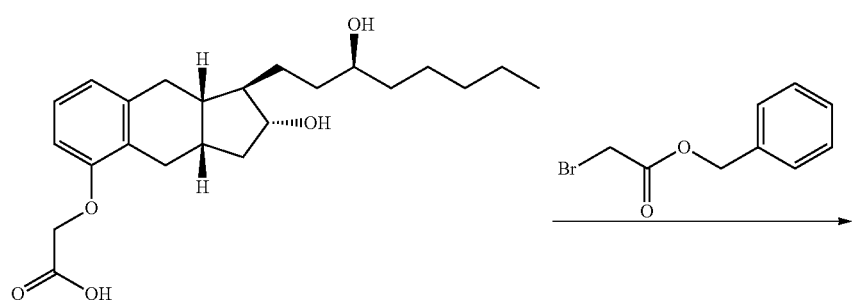

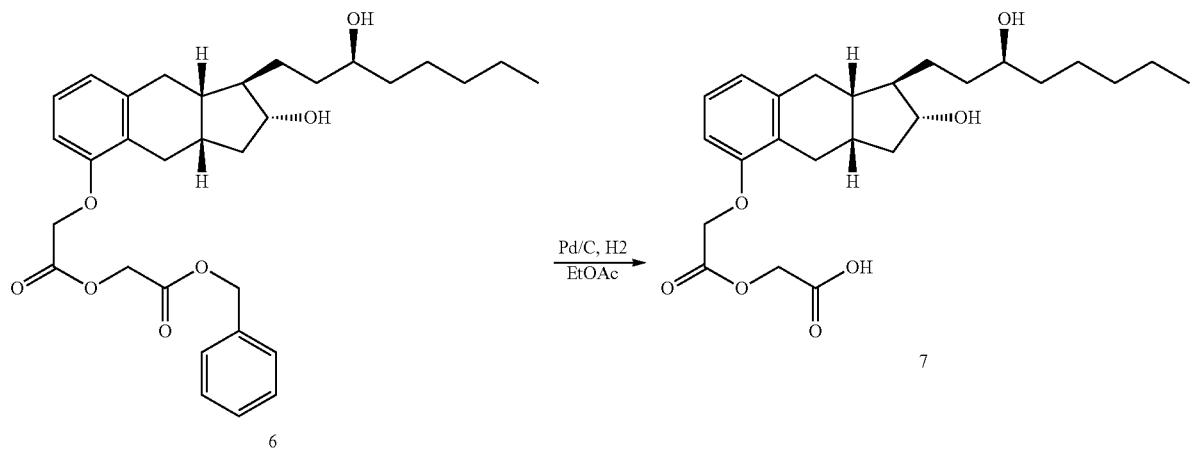

Synthesis of Treprostinil Acetoxy Acetate Benzyl Ester (6)

To a solution of treprostinil (5) (100.2 g, 256.58 mmol) in acetone (1.5 L) was added benzyl bromoacetate (44.3 mL, 282.23 mmol) potassium carbonate (106.4 g, 769.74 mmol). To this, acetone (800 mL) was added, and the mixture was stirred vigorously at room temperature under argon environment. After 64 h the reaction was found to be complete based on TLC. The reaction was filtered through celite and evaporated in vacuo to obtain crude treprostinil acetoxy acetate benzyl ester (6). This was purified by column chromatography using ethyl acetate:hexanes (0-60%) as mobile phase to obtain three fractions of treprostinil acetoxy acetate benzyl ester (6) (A: 6.4 g, B: 65.3 g, C: 50.2 g). The fraction C (50.2 g) was crystallized using ethyl acetate (400 mL) and hexane (100 mL) at 65° C. to obtain 28.1 g of product (6). The mother liquor (21.8 g) from this and fraction A (6.4 g) were combined and crystallized with ethyl acetate (170 mL) and hexane (60 mL) at 65 to 70° C. to obtain pure product (6) (26.7 g) (total, 120.1 g, 86.9% yield). The pure product was characterized by $^1$H NMR.

Synthesis of Treprostinil Acetoxy Acetate Acid (7)

To a solution (solubilized at 60° C.) of treprostinil benzyl acetoxy acetate (6) (73.5 g) in ethyl acetate (1.3 L) at RT was added palladium on carbon (7.3 g). Then tetrahydrofuran (100 mL) was added to keep the compound in solution. The reaction system was evacuated using vacuum and replaced with hydrogen gas under balloon pressure (three times). After 3 h of stirring at room temperature the reaction was found to be complete based on TLC. The reaction mixture was filtered through celite, split into two parts and evaporated in vacuo to obtain crude treprostinil acetoxy acetate acid (7) (43.5 g+45.7 g). These two batches were crystallized (separately) using tert-butyl methyl ether (250 mL) and hexanes (75 mL) at 40° C. They were combined and slurried in hexane (700 mL). The solid crystals were filtered through No. 4 filter paper and air dried to obtain pure treprostinil acetoxy acetate acid (7) (51.4 g, 83.9% yield) as white to off-white solid. The pure product was characterized by $^1$H NMR, $^{13}$C NMR, IR and MS. The melting point was found to be 92.5° C. to 95.2° C.

Example 2
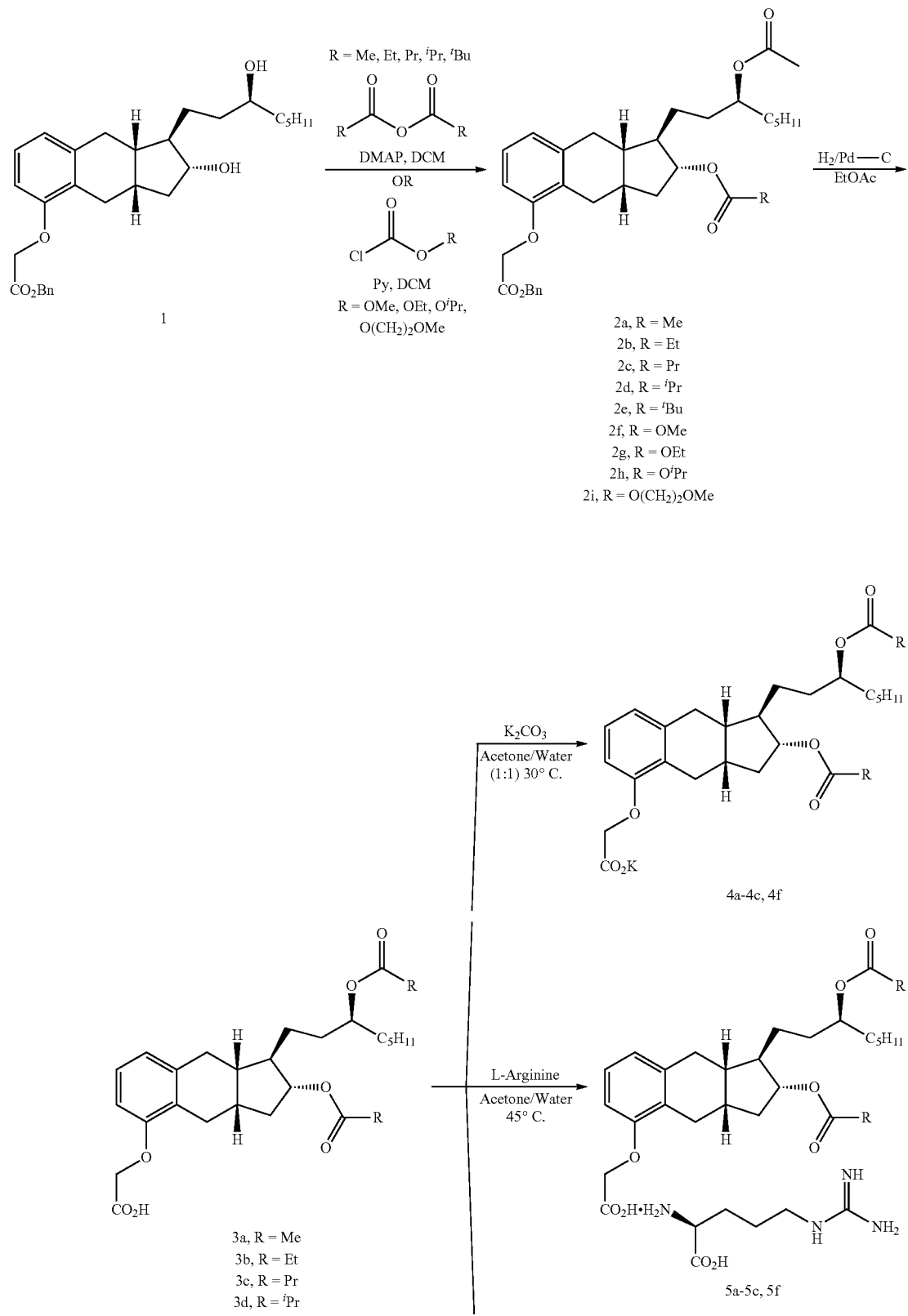
Scheme 3: Syntheses of Treprostinil Disubstituted Ester and Carbonate Salts 3e, R = ᵗBu
3f, R = OMe
3g, R = OEt
3h, R = OⁱPr
3i, R = O(CH₂)₂OMe
-continued
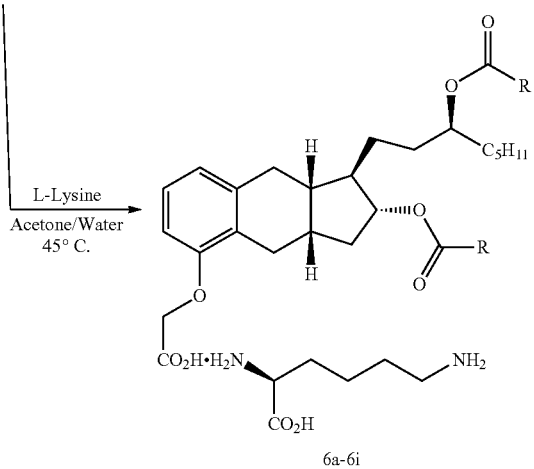
L-Lysine
Acetone/Water
45° C.
6a-6i
---
Scheme 4: Syntheses of Treprostinil Dialkylate and Disuccinamate L-Lysine Salts
---
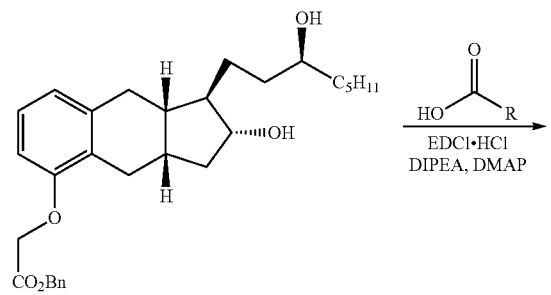
1
EDCl•HCl
DIPEA, DMAP
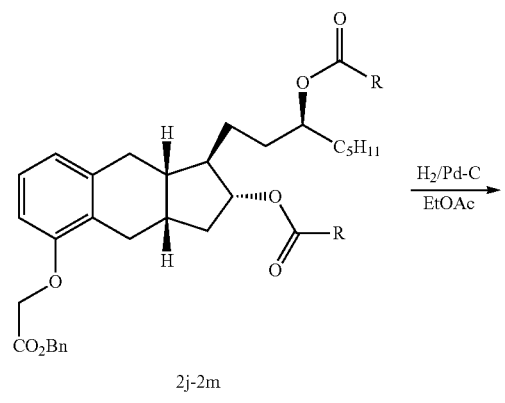
2j-2m
H₂/Pd-C
EtOAc -continued
Scheme 4: Syntheses of Treprostinil Dialkylate and Disuccinamate L-Lysine Salts
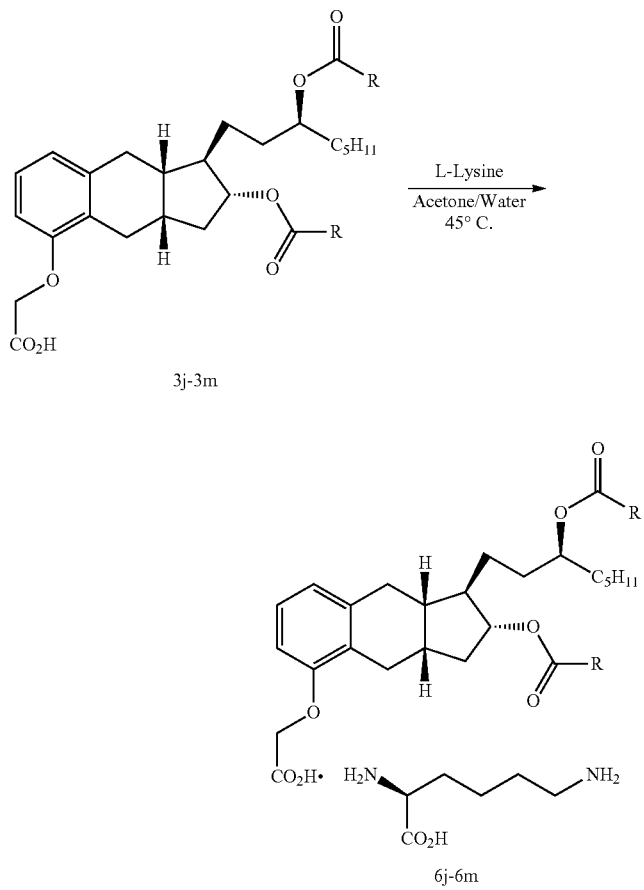
3j-3m
6j-6m
| Cmpd No. | R | Cmpd No. | R |
|---|---|---|---|
| 2j | CH₂OBn | 2l, 3l, 6l | 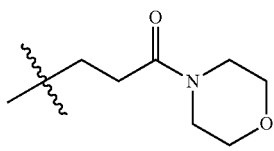 [SMILES: *CCC(=O)N1CCOCC1] |
| 3j, 6j | CH₂OH | | |
| 2k, 3k, 6k | | 2m, 3m, 6m | |
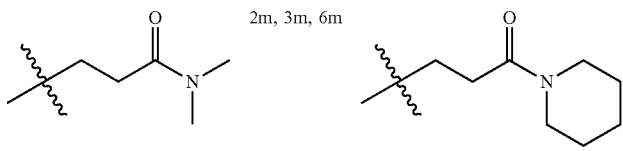

Scheme 5: Syntheses of Treprostinil Dicarbamate L-Lysine Salts

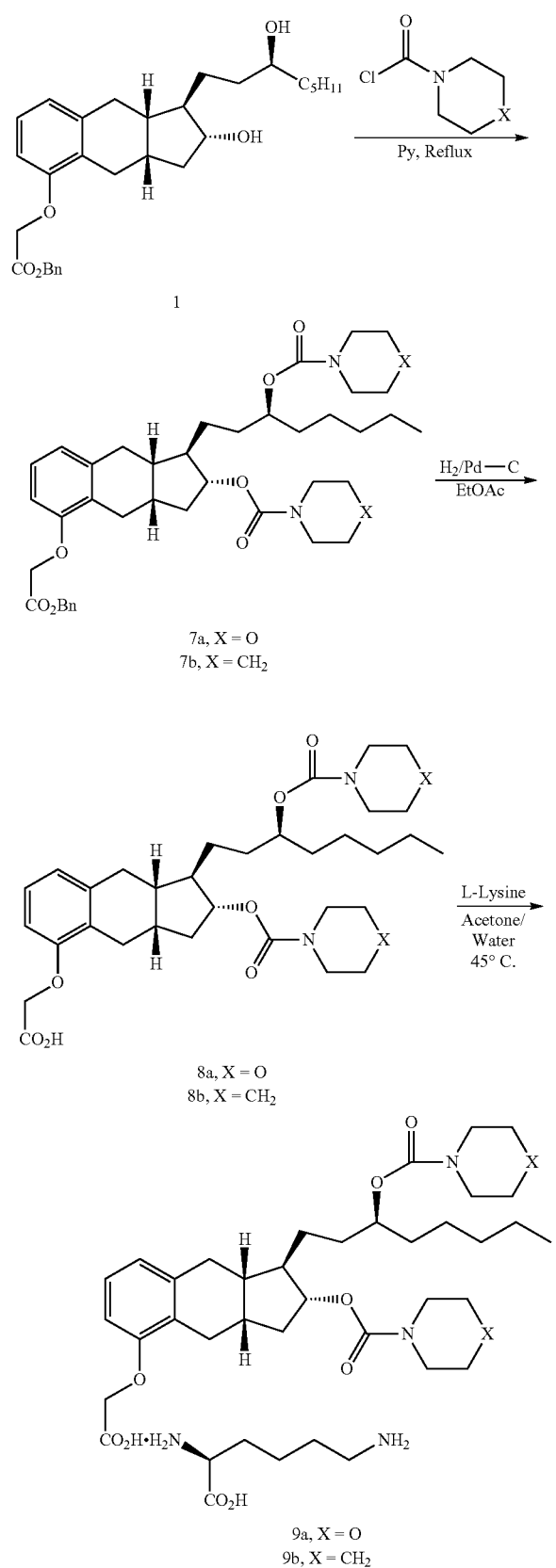

7a, X = O
7b, X = CH$_2$

8a, X = O
8b, X = CH$_2$

9a, X = O
9b, X = CH$_2$

General Experimental Procedures

General Procedure for the Synthesis of Treprostinil Dialkylate Benzyl Ester (2a-2e)

To a stirred solution of treprostinil benzyl ester (1) (1.0 eq.) in dichloromethane (DCM) was added DMAP (3.0 eq.) at room temperature under argon. The resulting reaction mixture was stirred for 5 min and then corresponding alkyl anhydride (3.0 eq.) was added slowly. After 1.5-4 h, TLC suggested that reaction was complete. Upon completion of the reaction, the reaction mixture was concentrated in vacuo and the crude compound was purified by silica-gel column chromatography (EtOAc/hexane) to afford pure treprostinil dialkylate benzyl ester (2a-2e). The compounds were characterized by IR, $^1$H NMR and LCMS.

General Procedure for the Synthesis of Treprostinil Alkyl Dicarbonate Benzyl Ester (2f-2i)

To a stirred solution of treprostinil benzyl ester (1) (1.0 eq.) in dichloromethane (DCM) and pyridine (1:1) at 0-5° C. (water+dry-ice) under argon was added a solution of corresponding alkyl chloroformate (2.5 eq.) in DCM dropwise. After 2-4 h, TLC suggested that reaction was complete. Upon completion of the reaction, the reaction mixture was concentrated in vacuo, dried under high vacuum and the resulting crude compound was purified by silica-gel column chromatography (EtOAc/hexane) to afford pure treprostinil alkyl dicarbonate benzyl ester (2f-2i). The compounds were characterized by IR, $^1$H NMR and LCMS.

General Procedure for the Synthesis of Treprostinil Dialkylate and Disuccinamate Benzyl Ester (2j-2m)

To a stirred solution of treprostinil benzyl ester (1) (1.0 eq.) and corresponding acid or succinamic acid (3.0 eq.) in dichloromethane (DCM) was added DIPEA (4.0 eq.) and DMAP (0.5 eq.) at room temperature under argon. Then EDCI.HCl (4.0 eq.) was added portionwise and the resulting reaction mixture was stirred overnight at room temperature under argon. After 16-65 h, TLC suggested that reaction was complete. Upon completion of the reaction, the reaction mixture was quenched with water, DCM layer was separated, and aqueous layer was extracted with DCM. Combined DCM layer was washed with brine, dried over anhydrous sodium sulfate (Na$_2$SO$_4$), filtered and concentrated in vacuo to afford crude material which was purified by silica-gel column chromatography (EtOAc/hexane) to afford pure treprostinil dialkylate or disuccinamate benzyl ester (2j-2m). The compounds were characterized by IR, $^1$H NMR and LCMS.

General Procedure for the Synthesis of Treprostinil Dicarbamate Benzyl Ester (7a-7b)

To a stirred solution of treprostinil benzyl ester (1) (1.0 eq.) in pyridine at room temperature under argon was added corresponding carbamoyl chloride (8.0 eq.). The resulting reaction mixture was refluxed under argon. After 24-40 h, TLC suggested that reaction was complete. Upon completion of the reaction, the reaction mixture was concentrated in vacuo, dried under high vacuum and the resulting crude compound was purified by silica-gel column chromatography (EtOAc/hexane) to afford pure treprostinil dicarbamate benzyl ester (7a-7b). The compounds were characterized by IR, $^1$H NMR and LCMS.

General Procedure for Hydrogenolysis to Synthesize Treprostinil Disubstituted Compounds (3a-3m, 8a-8b)

To a stirred solution of treprostinil disubstituted benzyl ester (2a-2m, 7a-7b) (1.0 eq.) in ethyl acetate (EtOAc) at room temperature was added 5% palladium on carbon (Pd—C, 50% water) (25-35 wt. % of 2a-2m, 7a-7b). The resulting reaction mixture was evacuated under house vacuum and replaced with hydrogen gas (filled in a 1 L balloon) for three times and then stirred at room temperature under hydrogen atmosphere. After 3-8 h, TLC suggested that reaction was complete. Upon completion of the reaction, the reaction mixture was filtered through a pad of celite, solids were washed with EtOAc and combined EtOAc layer was concentrated in vacuo, dried under high vacuum to afford pure treprostinil disubstituted compounds (3a-3m, 8a-8b). The compounds were characterized by IR, $^1$H NMR and LCMS.

General Procedure for the Synthesis Treprostinil Disubstituted Potassium Salts (4a-4c, 4f)

To a stirred solution of treprostinil disubstituted compound (3a-3c, 3f) (1.0 eq.) in acetone at 30° C. was added an aqueous solution of K$_2$CO$_3$ (0.5 eq.) dropwise. The resulting clear reaction mixture was stirred at 30-35° C. After 15-30 min, the reaction mixture was concentrated in vacuo and azeotropically dried with isopropyl acetate. The resulting viscous oil was triturated with heptane under sonication and concentrated in vacuo and dried under high vacuum at 35° C. (water bath) to afford treprostinil disubstituted potassium salts (4a-4c, 4f) as amorphous solid. The compounds were characterized by IR, $^1$H NMR and LCMS.

Compound 4a (Treprostinil Diacetate Potassium Salt): mp 228-232° C.; HPLC Purity: 100%

Compound 4b (Treprostinil Dipropionate Potassium Salt): mp 230-233° C.; HPLC Purity: 99.89%

Compound 4c (Treprostinil Dibutyrate Potassium Salt): mp 214-219° C.; HPLC Purity: 98.58%

Compound 4f (Treprostinil Methyl Dicarbonate Potassium Salt): mp 196-198° C.; HPLC Purity: 99.58%

General Procedure for the Synthesis Treprostinil Disubstituted L-Arginine Salts (5a-5c, 5f)

To a stirred solution of treprostinil disubstituted compound (3a-3c, 3f) (1.0 eq.) in isopropyl alcohol or acetone at 45° C. was added an aqueous solution of L-arginine (1.0 eq.) dropwise. The resulting clear reaction mixture was stirred at 45° C. After 30 min, the reaction mixture was concentrated under reduced pressure and azeotropically dried with isopropyl acetate. The resulting viscous oil was triturated with heptane under sonication and concentrated in vacuo and dried under high vacuum at 35° C. (water bath) to afford treprostinil disubstituted L-arginine salts (5a-5c, 5f) as amorphous solid. The compounds were characterized by IR, $^1$H NMR and LCMS.

Compound 5a (Treprostinil Diacetate L-Arginine Salt): mp 136-139° C.; HPLC Purity: 99.65%

Compound 5b (Treprostinil Dipropionate L-Arginine Salt): mp 210-213° C.; HPLC Purity: 99.79%

Compound 5c (Treprostinil Dibutyrate L-Arginine Salt): mp 195-198° C.; HPLC Purity: 98.67%

Compound 5f (Treprostinil Methyl Dicarbonate L-Arginine Salt): mp 184-186° C.; HPLC Purity: 98.66%

General Procedure for the Synthesis Treprostinil Disubstituted L-Lysine Salts (6a-6m, 9a-9b)

To a stirred solution of treprostinil disubstituted compound (3a-3m, 8a-8b) (1.0 eq.) in acetone at 45° C. was added an aqueous solution of L-lysine (1.0 eq.) dropwise. The resulting clear reaction mixture was stirred at 45° C. After 30 min, the reaction mixture was concentrated under reduced pressure and azeotropically dried with isopropyl acetate. The resulting viscous oil was triturated with heptane under sonication and concentrated in vacuo and dried under high vacuum at 35° C. (water bath) to afford treprostinil disubstituted L-lysine salts (6a-6m, 9a-9b) as amorphous solid. The compounds were characterized by IR, $^1$H NMR and LCMS.

Compound 6a (Treprostinil Diacetate L-Lysine Salt): mp 167-171° C.; HPLC Purity: 100%

Compound 6b (Treprostinil Dipropionate L-Lysine Salt): mp 179-182° C.; HPLC Purity: 99.67%

Compound 6c (Treprostinil Dibutyrate L-Lysine Salt): mp 178-181° C.; HPLC Purity: 98.65%

Compound 6d (Treprostinil Diisobutyrate L-Lysine Salt): mp 184-186° C.; HPLC Purity: 99.64%

Compound 6e (Treprostinil Dipivalate L-Lysine Salt): mp 182-184° C.; HPLC Purity: 98.78%

Compound 6f (Treprostinil Methyl Dicarbonate L-Lysine Salt): mp 173-176° C.; HPLC Purity: 99.68%

Compound 6g (Treprostinil Ethyl Dicarbonate L-Lysine Salt): mp 178-181° C.; HPLC Purity: 98.89%

Compound 6h (Treprostinil Isopropyl Dicarbonate L-Lysine Salt): mp 179-182° C.; HPLC Purity: 96.99%

Compound 6i (Treprostinil bis(2-Methoxyethylcarbonate) L-Lysine Salt): mp 178-181° C.; HPLC Purity: 100%

Compound 6j (Treprostinil Dihydroxyacetate L-Lysine Salt): mp 108-111° C.; HPLC Purity: 97.18%

Compound 6k (Treprostinil bis(Dimethylsuccinamate) L-Lysine Salt): mp 147-150° C.; HPLC Purity: 95.84%

Compound 6l (Treprostinil bis(Morpholinosuccinamate) L-Lysine Salt): mp 146-149° C.; HPLC Purity: 98.66%

Compound 6m (Treprostinil bis(Piperidinylsuccinamate) L-Lysine Salt): mp 135-138° C.; HPLC Purity: 95.42%

Compound 9a (Treprostinil Dimorpholinocarbamate L-Lysine Salt): mp 145-148° C.; HPLC Purity: 97.74%

Compound 9b (Treprostinil Dipiperidinylcarbamate L-Lysine Salt): mp 165-167° C.; HPLC Purity: 93.81%

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention.

All of the publications, patent applications and patents cited in this specification are incorporated herein by reference in their entirety.

What is claimed is:

1. A compound having the following formula:

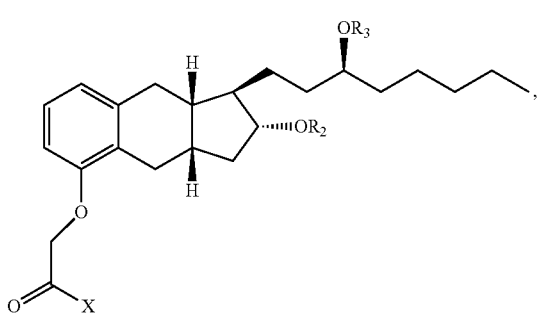

wherein X is a salt moiety or a promoiety; wherein each of $OR_2$ and $OR_3$ has a lower reactivity with a carboxyl group than that of the respective hydroxyl group of unsubstituted treprostinil and C=OX has a lower reactivity with hydroxyl than that of the carboxyl group of unsubstituted treprostinil, wherein $R_2$ and $R_3$ are each independently selected from $CH_2OBn$, $CH_2OH$,

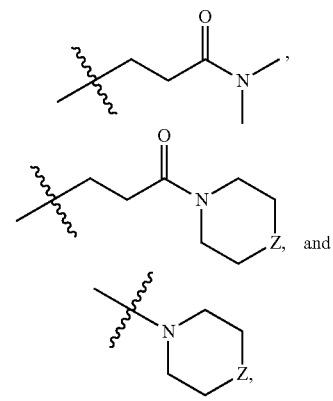

wherein Z is O or $CH_2$; or wherein $R_2$ and $R_3$ are joined together to form an 8-12 membered heterocyclyl comprising —C(O)—, —$SO_2$—, or

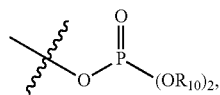

and wherein
each $R_{10}$ is H, optionally substituted $C_1$-$C_6$ alkyl, optionally substituted $C_1$-$C_6$ alkenyl, optionally substituted cycloalkyl, optionally substituted heteroaryl, or optionally substituted aryl.

2. The compound of claim 1, wherein X is $O^-$·a salt counterion.

3. The compound of claim 1, wherein X is $O^-$·a salt counterion of an amino acid.

4. The compound of claim 3, wherein the amino acid is arginine or lysine.

5. The compound of claim 1, wherein X is the promoiety.

6. The compound of claim 5, wherein X is $OR_9$ or $NR_1R_6$; wherein $R_9$ is alkyl chain $C_1$-$C_{20}$,

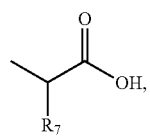

wherein $R_1$ is H or $C_1$-$C_4$ alkyl and $R_6$ is

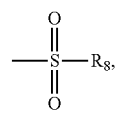

$R_7$ is H or $C_1$-$C_4$ alkyl.

7. The compound of claim 6, wherein X is $OR_9$ and $R_9$ is

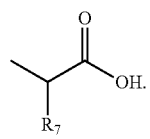

8. The compound of claim 6, wherein X is $NR_1R_6$, $R_1$ is H and $R_6$ is

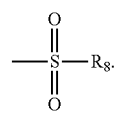

9. The compound of claim 1, wherein
or $R_2$ and $R_3$ are joined together to form an 8-12 membered heterocyclyl comprising
—C(O)—, —$SO_2$—, or

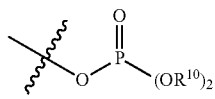

wherein
each $R_{10}$ is H, optionally substituted $C_1$-$C_6$ alkyl, optionally substituted $C_1$-$C_6$ alkenyl, optionally substituted cycloalkyl, optionally substituted heteroaryl, or optionally substituted aryl.

10. The compound of claim 1, wherein $R_2$ and $R_3$ are each independently selected from $CH_2OBn$, $CH_2OH$,

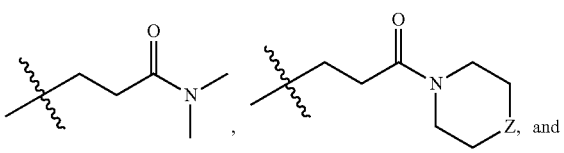

-continued

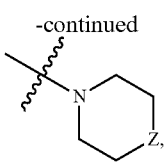

wherein Z is O or $CH_2$.

11. The compound of claim 1, wherein $R_2$ and $R_3$ are the same.

12. The compound of claim 1, wherein $R_2$ and $R_3$ are joined together to form an 8-12 membered heterocyclyl comprising —C(O)—.

13. The compound of claim 1, which is a water soluble compound.

14. The compound of claim 1, wherein the compound is selected from the group consisting of:

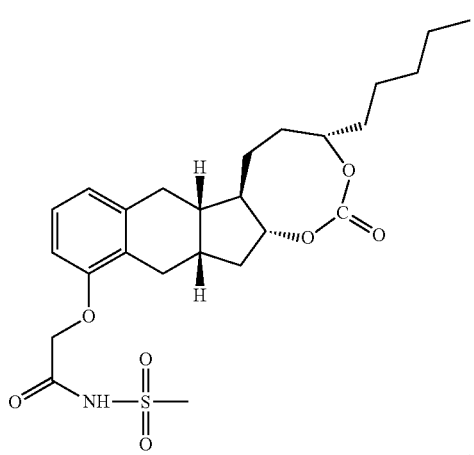

15. The compound of claim 1, wherein each of $R_2$ and $R_3$ is selected from the group consisting of

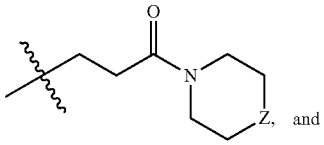  and

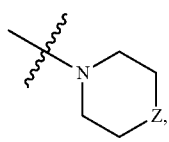

wherein Z is O or $CH_2$.

16. The compound of claim 15, wherein each of $R_2$ and $R_3$ is

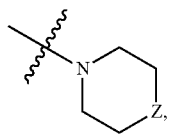

wherein Z is O or $CH_2$.

17. The compound of claim 16, wherein Z is O.
18. The compound of claim 16, wherein Z is $CH_2$.
19. The compound of claim 16, wherein X is L-lysine.
20. The compound of claim 15, wherein X is L-lysine.
21. The compound of claim 1, wherein the compound is selected from the group consisting of treprostinil bis(dimethylsuccinamate) L-lysine salt; treprostinil bis(morpholinosuccinamate) L-lysine salt; treprostinil bis(piperidinylsuccinamate) L-lysine salt; treprostinil dimorpholinocarbamate L-lysine salt; and treprostinil dipiperidinylcarbamate L-lysine salt.

* * * * *